(12) United States Patent
Lo et al.

(10) Patent No.: US 10,900,080 B2
(45) Date of Patent: Jan. 26, 2021

(54) MOLECULAR TESTING OF MULTIPLE PREGNANCIES

(75) Inventors: Yuk Ming Dennis Lo, Homantin (HK); Wai Kwun Rossa Chu, Shatin (HK); Kwan Chee Chan, Mei Foo Sun Chuen (HK); Tak Yeung Leung, Shatin (HK); Peiyong Jiang, Shatin (HK)

(73) Assignee: The Chinese University of Hong Kong, New Territories (HK)

(*) Notice: Subject to any disclaimer, the term of this patent is extended or adjusted under 35 U.S.C. 154(b) by 0 days.

(21) Appl. No.: 13/405,073

(22) Filed: Feb. 24, 2012

(65) Prior Publication Data

US 2013/0059733 A1    Mar. 7, 2013

Related U.S. Application Data

(60) Provisional application No. 61/446,256, filed on Feb. 24, 2011.

(51) Int. Cl.
| | |
|---|---|
| *C12Q 1/6881* | (2018.01) |
| *G16B 40/00* | (2019.01) |
| *G16B 20/00* | (2019.01) |

(52) U.S. Cl.
CPC .......... *C12Q 1/6881* (2013.01); *G16B 20/00* (2019.02); *C12Q 2600/154* (2013.01); *C12Q 2600/156* (2013.01); *C12Q 2600/172* (2013.01); *G16B 40/00* (2019.02)

(58) Field of Classification Search
CPC ........ C12Q 2600/156; C12Q 2600/172; C12Q 2600/106; C12Q 2600/16; C12Q 1/6876; C12Q 1/68; C12Q 1/6806; G01N 33/6893; G06F 19/18; G06F 19/22; G06F 19/3431
See application file for complete search history.

(56) References Cited

U.S. PATENT DOCUMENTS

| | | | |
|---|---|---|---|
| 6,342,355 B1 | 1/2002 | Hacia | |
| 7,332,277 B2 | 2/2008 | Dhallan | |
| 2004/0185495 A1 | 9/2004 | Schueler et al. | |
| 2008/0070792 A1 | 3/2008 | Stoughton et al. | |
| 2009/0029377 A1* | 1/2009 | Lo | G06F 19/18 435/6.11 |
| 2010/0105049 A1 | 4/2010 | Ehrich | |
| 2010/0216153 A1 | 8/2010 | Lapidus et al. | |
| 2011/0086769 A1* | 4/2011 | Oliphant | C12Q 1/6806 506/9 |
| 2011/0105353 A1 | 5/2011 | Lo | |
| 2011/0312503 A1* | 12/2011 | Chuu | C12Q 1/6869 506/2 |
| 2013/0029852 A1 | 1/2013 | Rava et al. | |
| 2013/0059733 A1 | 3/2013 | Lo et al. | |

FOREIGN PATENT DOCUMENTS

| | | |
|---|---|---|
| CN | 102770558 A | 11/2012 |
| JP | 2008-504837 A | 2/2008 |
| JP | 2010-43063 A | 2/2010 |
| TW | 201243326 A | 11/2012 |
| WO | 2003/031646 A1 | 4/2003 |
| WO | 2010/075459 A1 | 1/2010 |
| WO | 2011/057094 A1 | 5/2011 |
| WO | 2012/103031 A2 | 8/2012 |
| WO | 2012/108920 A1 | 8/2012 |
| WO | 2012/141712 A1 | 10/2012 |
| WO | 2012/142334 A2 | 10/2012 |
| WO | 2013/052913 A2 | 4/2013 |
| WO | 2014139477 A1 | 9/2014 |

OTHER PUBLICATIONS

Chim et al (PNAS. 2005. 102: 14753-14758).*
Chiu (The American Journal of Pathology. Mar. 2007. 170: 941-950).*
Bianchi (Clinical Chemistry. 2001. 47: 1867-1869).*
Lun et al (Clinical Chemistry. 2007. 53: 796-798).*
Illanes (Prenatal Diagnosis. 2006. 26: 1216-1218).*
Majer (Prenatal Diagnosis. 2007. 27: 1219-1223).*
Attilakos, George, et al., "Quantification of free fetal DNA in multiple pregnancies and relationship with chorionicity," Prenatal Diagnosis, 2011, pp. 967-972, vol. 31.
Finning, K.M, et al., "Prediction of fetal D status from maternal plasma: introduction of a new noninvasive fetal RHD genotyping service," Transfusion, Aug. 2002, pp. 1079-1085, vol. 42.
Ghanta, Sujana, et al., "Non-Invasive Prenatal Detection of Trisomy 21 Using Tandem Single Nucleotide Polymorphisms," PloS One, Oct. 2010, 10 pages, vol. 5, Issue 10.
Smid, Maddalena, et al., "Fetal DNA in Maternal Plasma in Twin Pregnancies," Clinical Chemistry, 2003, pp. 1526-1528, vol. 49, No. 9.
Tungwiwat, W., et al., "Non-invasive fetal sex determination using a conventional nested PCR analysis of fetal DNA in maternal plasma," Clinica Chimica Acta, 2003, vol. 334, pp. 173-177.
Pertl, B., et al., "Detection of male and female fetal DNA in maternal plasma by multiplex fluorescent polymerase chain reaction amplification of short tandem repeats," Human Genetics, 2000, vol. 106, pp. 45-49.
Guilherme, R., et al., "Zygosity and chorionicity in triplet pregnancies: new data," Human Reproduction, 2009, vol. 24, pp. 100-105.
Chan, F.Y., et al., "Prenatal RHD gene determination and dosage analysis by PCR: clinical evaluation," Prenatal Diagnosis, 2001, vol. 21, pp. 321-326.
International Search Report and Written Opinion dated Aug. 31, 2012 in PCT/IB2012/000344, 10 pages.

(Continued)

*Primary Examiner* — Katherine D Salmon
(74) *Attorney, Agent, or Firm* — Kilpatrick Townsend & Stockton LLP

(57) ABSTRACT

Methods, systems, and apparatus are provided for determining zygosity of a multiple-fetus pregnancy using a biological sample taken from the mother. The fetal and maternal DNA in the sample (e.g. plasma) can be analyzed for a particular chromosomal region to identify genetic differences in the fetuses. For example, a normalized parameter for the measure of a primary or secondary allele can show variances for different chromosomal regions when fetuses are dizygotic. Such a variance can be determined relative to an expected value if the fetuses were genetically identical. Statistical methods are provided for analyzing the variation of the normalized parameters to determine fetal DNA concentration and the maternal-fetal mixed genotype at various loci. Parental genotype and haplotype information can also be used to identify inheritance of different parental haplotypes to indicate genetic differences among the fetuses.

49 Claims, 20 Drawing Sheets

(56) References Cited

OTHER PUBLICATIONS

Office Action dated Apr. 21, 2015 in Japanese Patent Application No. 2013-554948, 9 pages.
International Search Report and Written Opinion dated Jun. 27, 2014 in PCT/CN2014/073506, 15 pages.
Dhallan, R.S., et al., "A non-invasive test for prenatal diagnosis based on fetal DNA present in maternal blood: a preliminary study," The Lancet, Feb. 1, 2007, vol. 369, pp. 474-481.
Lun, F.M.F., et al., "Noninvasive prenatal diagnosis of monogenic diseases by digital size selection and relative mutation dosage on DNA in maternal plasma," Proceedings of the National Academy of Sciences, Dec. 16, 2008, vol. 105, No. 50, pp. 19920-19925.
Ding, C., et al., "MS Analysis of single-nucleotide differences in circulating nucleic acids: Application to noninvasive prenatal diagnosis," Proceedings of the National Academy of Sciences, Jul. 20, 2004, vol. 101, No. 29, pp. 10762-10767.
European Search Report dated Mar. 17, 2015 in EP14193704, 15 pages.
Canick, Jacob a. et al.; "DNA sequencing of maternal plasma to identify Down syndrome and other trisomies in multiple gestations"; Prenatal Diagnosis; 2012; 32; pp. 730-734.
Lau, Tze Kin et al.; "Non-invasive prenatal screening of fetal Down syndrome by maternal plasma DNA sequencing in twin pregnancies"; The Journal of Maternal-Fetal and Neonatal Medicine; 2013; 26(4); pp. 434-437 (7 pages).
Extended European Search Report dated Sep. 28, 2016 in EP Patent Application No. 14764129.4. 9 pages.
Kitzman, Jacob O. et al.; "Noninvasive Whole-Genome Sequencing of a Human Fetus"; Science Translational Medicine; Jun. 6, 2012; vol. 4, Issue 137; 137ra76; 19 pages.
English translation of Search Report included in Office Action dated Jan. 4, 2016 in TW Patent Application 101106446, filed Feb. 24, 2012. 1 page.
Chen, C.P., et al., "Rapid determination of zygosity and common aneuploidies from amniotic fluid cells using quantitative fluorescent polymerase chain reaction following genetic amniocentesis in multiple pregnancies," Human Reproduction, Apr. 1, 2000, vol. 15, No. 4, pp. 929-934.
Sehnert, A.J., et al., "Optimal Detection of Fetal Chromosomal Abnormalities by Massively Parallel DNA Sequencing of Cell-Free Fetal DNA from Maternal Blood," Clinical Chemistry. Jul. 1, 2011, vol. 57, No. 7, pp. 1042-1049.
Orendi, K., et al., "SRY-specific cell free fetal DNA in maternal plasma in twin pregnancies throughout gestation," Placenta, Mar. 23, 2011, vol. 32, No. 8, pp. 611-615.
Qu, J.Z.Z., et al., "Noninvasive Prenatal Determination of Twin Zygosity by Maternal Plasma DNA Analysis," Clinical Chemistry, Feb. 1, 2013, vol. 59, No. 2, pp. 427-435.
Supplementary European Search Report dated Sep. 19, 2014 in European Patent Application No. EP 12834099, 10 pages.

\* cited by examiner

Monozygotic Twins

|  | Mother | | Father | |
|---|---|---|---|---|
|  | HapI | HapII | HapIII | HapIV |
| Locus 1 | A | A | A | C |
| Locus 2 | T | T | G | T |

|  | Twin 1 | | Twin 2 | |
|---|---|---|---|---|
|  | HapI | HapIII | HapI | HapIII |
| Locus 1 | A | A | A | A |
| Locus 2 | T | G | T | G |

Dizygotic Twins

|  | Mother | | Father | |
|---|---|---|---|---|
|  | HapI | HapII | HapIII | HapIV |
| Locus 1 | A | A | A | C |
| Locus 2 | T | T | G | T |

|  | Twin 1 | | Twin 2 | |
|---|---|---|---|---|
|  | HapI | HapIII | HapI | HapIV |
| Locus 1 | A | A | A | C |
| Locus 2 | T | G | T | T |

FIG. 2A

Monozygotic Twins

| | Mother | | Father | |
|---|---|---|---|---|
| | Allele I | Allele II | Allele III | Allele IV |
| No. of repeats | 4 | 7 | 5 | 8 |

| | Twin 1 | | Twin 2 | |
|---|---|---|---|---|
| | Allele I | Allele III | Allele I | Allele III |
| No. of repeats | 4 | 5 | 4 | 5 |

Dizygotic Twins

| | Mother | | Father | |
|---|---|---|---|---|
| | Allele I | Allele II | Allele III | Allele IV |
| No. of repeats | 4 | 7 | 5 | 8 |

| | Twin 1 | | Twin 2 | |
|---|---|---|---|---|
| | Allele I | Allele III | Allele II | Allele IV |
| No. of repeats | 4 | 5 | 7 | 8 |

- 410 — Determine genotype of the pregnant female at each of one or more first loci within a first chromosomal region – genotypes for first loci are all homozygous or all heterozygous

- 420 — Detect primary allele (more abundant) and/or secondary allele (less abundant) in the biological sample at each of the first loci

- 430 — Measure, at the one or more first loci, a first amount of the one or more primary alleles and/or a second amount of the one or more secondary alleles in the biological sample

- 440 — Obtain a normalized parameter for the first amount or the second amount

- 450 — Compare the normalized parameter to a cutoff value to determine if the normalized parameter is statistically different from an expected value if the fetuses are genetically identical for the first chromosomal region

- 460 — Determine whether two fetuses of the pregnant female are dizygotic based on the comparison of the normalized parameter to the cutoff value

| Locus 1 | | |
|---|---|---|
| Mother | | Father |
| A | A | A T |
| Twin 1 | | Twin 2 |
| A | T | A T |

Monozygotic Twins

| Locus 2 | | |
|---|---|---|
| Mother | | Father |
| G | G | G C |
| Twin 1 | | Twin 2 |
| G | C | G C |

Maternal plasma

| | Locus 1 | | Locus 2 | |
|---|---|---|---|---|
| Mother | A 80 | A 80 | G 80 | G 80 |
| Twin 1 | A 10 | T 10 | G 10 | C 10 |
| Twin 2 | A 10 | T 10 | G 10 | C 10 |
| Total | A 180 | T 20 | G 180 | C 20 |

Dizygotic Twins

Locus 1

| | Mother | Father |
|---|---|---|
| | A  A | A  T |
| | Twin 1 | Twin 2 |
| | A  T | A  T |

Locus 2

| | Mother | Father |
|---|---|---|
| | G  G | G  C |
| | Twin 1 | Twin 2 |
| | G  G | G  C |

Maternal plasma

| | Locus 1 | | Locus 2 | |
|---|---|---|---|---|
| Mother | A 80 | A 80 | G 80 | G 80 |
| Twin 1 | A 10 | T 10 | G 10 | G 10 |
| Twin 2 | A 10 | T 10 | G 10 | C 10 |
| Total | A 180 | T 20 | G 190 | C 10 |

FIG. 7

|  | Whole Genome | | Target Region | |
|---|---|---|---|---|
| Genotype: Mother/Twins I-Twins II | SNP Number | Percentage (%) | SNP Number | Percentage (%) |
| AA/AA-AA | 529473 | 59.72 | 9248 | 34.71 |
| AA/AA-AB | 33180 | 3.74 | 1098 | 4.12 |
| AA/AB-AA | 33766 | 3.81 | 1130 | 4.24 |
| AA/AB-AB | 71528 | 8.07 | 4312 | 16.18 |
| AB/AA-AA | 34299 | 3.87 | 1739 | 6.53 |
| AB/AA-AB | 61030 | 6.88 | 3243 | 12.17 |
| AB/AA-BB | 17067 | 1.93 | 375 | 1.41 |
| AB/AB-AA | 61374 | 6.92 | 3174 | 11.91 |
| AB/AB-AB | 43967 | 4.96 | 2291 | 8.60 |

|  | Whole Genome | | Target Region | |
|---|---|---|---|---|
| Genotype: Mother/Fetus | SNP Number | Percentage (%) | SNP Number | Percentage (%) |
| AA/AA | 573422 | 63.92 | 10437 | 38.96 |
| AA/AB | 105511 | 11.76 | 5812 | 21.70 |
| AB/AA | 114057 | 12.72 | 5408 | 20.19 |
| AB/AB | 103518 | 11.54 | 5111 | 19.08 |

| Total SNP | Same Genotype | Different Genotype | Same Genotype (%) | Different Genotype (%) |
|---|---|---|---|---|
| 890062 | 682107 | 207955 | 76.64 | 23.36 |

| chromosome | DCDA (%) | MCDA (%) |
|---|---|---|
| chr1 | 23.79 | 17.48 |
| chr2 | 15.80 | 15.69 |
| chr3 | 14.88 | 16.25 |
| chr4 | 23.30 | 17.70 |
| chr5 | 22.25 | 15.85 |
| chr7 | 24.50 | 11.83 |
| chr8 | 17.53 | 15.86 |
| chr9 | 22.29 | 18.31 |
| chr13 | 22.05 | 16.54 |
| chr15 | 22.47 | 16.54 |
| chr17 | 22.26 | 16.02 |
| chr19 | 15.15 | 17.03 |
| chr20 | 18.65 | 15.17 |
| chr22 | 21.90 | 16.54 |
| SD | 3.36 | 1.52 |

FIG. 12D

| Chromosome | DCDA (%) | MCDA (%) |
|---|---|---|
| chr1 | 21.42 | 16.37 |
| chr2 | 15.37 | 13.60 |
| chr3 | 14.45 | 14.06 |
| chr4 | 20.07 | 14.95 |
| chr5 | 18.63 | 14.17 |
| chr7 | 15.82 | 12.05 |
| chr8 | 16.91 | 14.37 |
| chr9 | 19.27 | 14.81 |
| chr12 | 19.28 | 12.53 |
| chr13 | 19.88 | 14.54 |
| chr15 | 19.76 | 13.46 |
| chr17 | 19.64 | 14.81 |
| chr19 | 15.48 | 14.75 |
| chr20 | 16.33 | 14.13 |
| chr22 | 18.73 | 15.71 |
| SD | 2.14 | 1.10 |

FIG. 12E

MOLECULAR TESTING OF MULTIPLE PREGNANCIES

CROSS-REFERENCES TO RELATED APPLICATIONS

The present application claims priority from and is a non provisional application of U.S. Provisional Application No. 61/446,256, entitled "MOLECULAR TESTING OF TWIN PREGNANCIES" filed Feb. 24, 2011, the entire contents of which is herein incorporated by reference for all purposes.

This application is related to commonly owned U.S. patent application Ser. No. 12/940,993 entitled "Fetal Genomic Analysis From A Maternal Biological Sample" by Lo et al., filed Nov. 5, 2010, the disclosure of which is incorporated by reference in its entirety.

BACKGROUND

A multiple pregnancy refers to a pregnancy in which more than one fetus is carried by a pregnant woman. Twin pregnancies are the most common form of multiple pregnancies. Monozygotic twins refer to a pair of twins who are derived from the same fertilized egg. Therefore, the pair of twins have identical genetic makeup across the whole genome. Dizygotic twins are a pair of twins that are derived from two different fertilized eggs. The genetic makeup of the pair of twins would not be identical. Instead, the similarity of genetic makeup of this pair of twins would resemble a pair of siblings who are born at different times.

Information concerning the zygosity of twin pregnancies has conventionally been obtained by ultrasound scanning (Chauhan S P et al. *Am J Obstet Gynecol* 2010; 203: 305-315) or invasive prenatal diagnosis (e.g. amniocentesis) (Chen C P et al. *Hum Reprod* 2000; 15: 929-934). Such zygosity information is useful for subsequent obstetric management. For example, in the event that amniocentesis is performed for aneuploidy detection, a pregnancy involving dizygotic twins would require the individual sampling of each amniotic sac. For a monozygotic twin pregnancy involving two amniotic sacs, theoretically only the sampling of one of the two amniotic sacs would be needed. However, ultrasound scanning can be inaccurate or be limited (e.g. the fetuses are of different sex), and the invasive prenatal diagnosis can result in harm to the fetus and/or mother.

Accordingly, it is desirable for new techniques to provide zygosity information for a pregnancy with multiple fetuses.

BRIEF SUMMARY

Embodiments of the present invention provide methods, systems, and apparatus for determining zygosity of a multiple-fetus pregnancy using a biological sample taken from the mother, which is non-invasive to the fetuses. The fetal and maternal DNA in the sample (e.g. plasma) can be analyzed for a particular chromosomal region to identify genetic differences in the fetuses. For example, a normalized parameter for the measure of a primary or secondary allele can show variances for different chromosomal regions when fetuses are dizygotic. Such a variance can be determined relative to an expected value if the fetuses were genetically identical. Statistical methods are provided for analyzing the variation of the normalized parameters to determine fetal DNA concentration and the maternal-fetal mixed genotype at various loci. Parental genotype and haplotype information can also be used to identify inheritance of different parental haplotypes to indicate genetic differences among the fetuses.

Among other benefits, the determination of the zygosity of multiple pregnancies can aid the use of noninvasive prenatal testing procedures done, for example, using maternal blood.

According to one embodiment, a method for analyzing a biological sample of a female pregnant with a plurality of fetuses to determine whether at least two fetuses of a pregnant female are dizygotic. The biological sample comprises fetal and maternal DNA. A genotype of the pregnant female is determined at each of one or more first loci within a first chromosomal region. The mother is homozygous at each of the first loci or is heterozygous at each of the first loci. Each of the first loci exhibits a respective primary allele and a respective secondary allele in the biological sample. The respective primary allele is more abundant than the respective secondary allele for each of the first loci. A first amount of the one or more primary alleles and/or a second amount of the one or more secondary alleles are measured in the biological sample at the one or more first loci. A normalized parameter is obtained for the first amount or the second amount. The normalized parameter is compared to a cutoff value to determine if the normalized parameter is statistically different from an expected value if the fetuses are genetically identical for the first chromosomal region. The expected value is obtained from a measurement of the biological sample. Whether at least two fetuses of the pregnant female are dizygotic is determined based on the comparison of the normalized parameter to the cutoff value.

According to another embodiment, a first amount of one or more fetal-specific sequences are measured in the biological sample measuring at one or more first loci. A normalized parameter is obtained for the first amount. The normalized parameter is compared to a cutoff value to determine if the normalized parameter is statistically different from an expected value if the fetuses are genetically identical for the first chromosomal region. The expected value is obtained from a measurement of the biological sample. Then, it is determined whether at least two fetuses of the pregnant female are dizygotic based on the comparison of the normalized parameter to the cutoff value.

According to another embodiment, for each of a plurality of chromosomal regions, one or more alleles are measured in the biological sample at each of one or more loci in the respective chromosomal region, and a respective amount of each measured allele is determined at each locus. Whether at least two of the fetuses have inherited a different haplotype of the respective chromosomal region from a first parent is determined based on the respective amounts of the measured alleles. A first amount of the chromosomal regions where at least two of the fetuses have inherited a different haplotype from the first parent is determined. The first amount is compared to one or more cutoff values to determine whether at least two of the fetuses are dizygotic.

According to another embodiment, a histogram is created as follows. For each of a plurality of chromosomal regions: one or more loci in the respective chromosomal region are identified at which a respective first allele and a respective second allele are detected in the biological sample, a first amount of the one or more first alleles and/or a second amount of the one or more second alleles are measured in the biological sample at the one or more loci, and a normalized parameter is obtained for the first amount or the second amount. Counters of the histogram are incremented based on a number of chromosomal regions with specified values for the normalized parameter. Chromosomal regions corresponding to loci at which the mother is homozygous and at least one of the fetuses is heterozygous or corresponding to loci at which the mother is heterozygous and at least one of the fetuses is homozygous are identified. A multi-component mixture model is fit to the histogram corresponding to the identified chromosomal regions. The multi-component mixture model includes a mixture coefficient for each of a plurality of components. It is determined whether at least two of the fetuses are dizygotic using at least two of the mixture coefficients.

According to another embodiment, a method of determining a fetal DNA percentage in a biological sample from a pregnant female with at least two fetuses is provided. For each of a plurality of chromosomal regions: one or more loci in the respective chromosomal region are identified at which a respective first allele and a respective second allele are detected in the biological sample, a first amount of the one or more first alleles and/or a second amount of the one or more second alleles are measured in the biological sample at the one or more loci, and a normalized parameter is obtained for the first amount or the second amount. Counters of the histogram are incremented based on a number of chromosomal regions with specified values for the normalized parameter. A linear combination of probability distributions is fit to the histogram, where the fetal DNA percentage is an input to the linear combination of probability distributions. The input fetal DNA percentage is varied to find an optimal fetal DNA percentage that optimizes a fit of the linear combination of probability distributions to the histogram.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIGS. 2A and 2B show examples for determining the zygosity of the fetuses when one knows the haplotypes of the parents at two loci for a given chromosomal region. FIG. 2A shows an example where the mother is homozygous at the two loci and the father is heterozygous. FIG. 2B shows an example where the mother is heterozygous at the two loci and the father is homozygous.

FIG. 3 also shows an example of microsatellite analysis where a locus has four different alleles.

FIG. 4 is a flowchart illustrating a method 400 for analyzing a biological sample of a female pregnant with a plurality of fetuses to determine whether at least two fetuses of a pregnant female are genetically different for a first chromosomal region according to embodiments of the present invention.

FIGS. 6 and 7 illustrate using regional genomic variations in fetal DNA fractions in maternal plasma to reveal the zygosity of twin pregnancies according to embodiments of the present invention.

FIGS. 12A-12E are tables showing results of the deductive SNP analysis according to embodiments of the present invention.

DEFINITIONS

Figure 1:
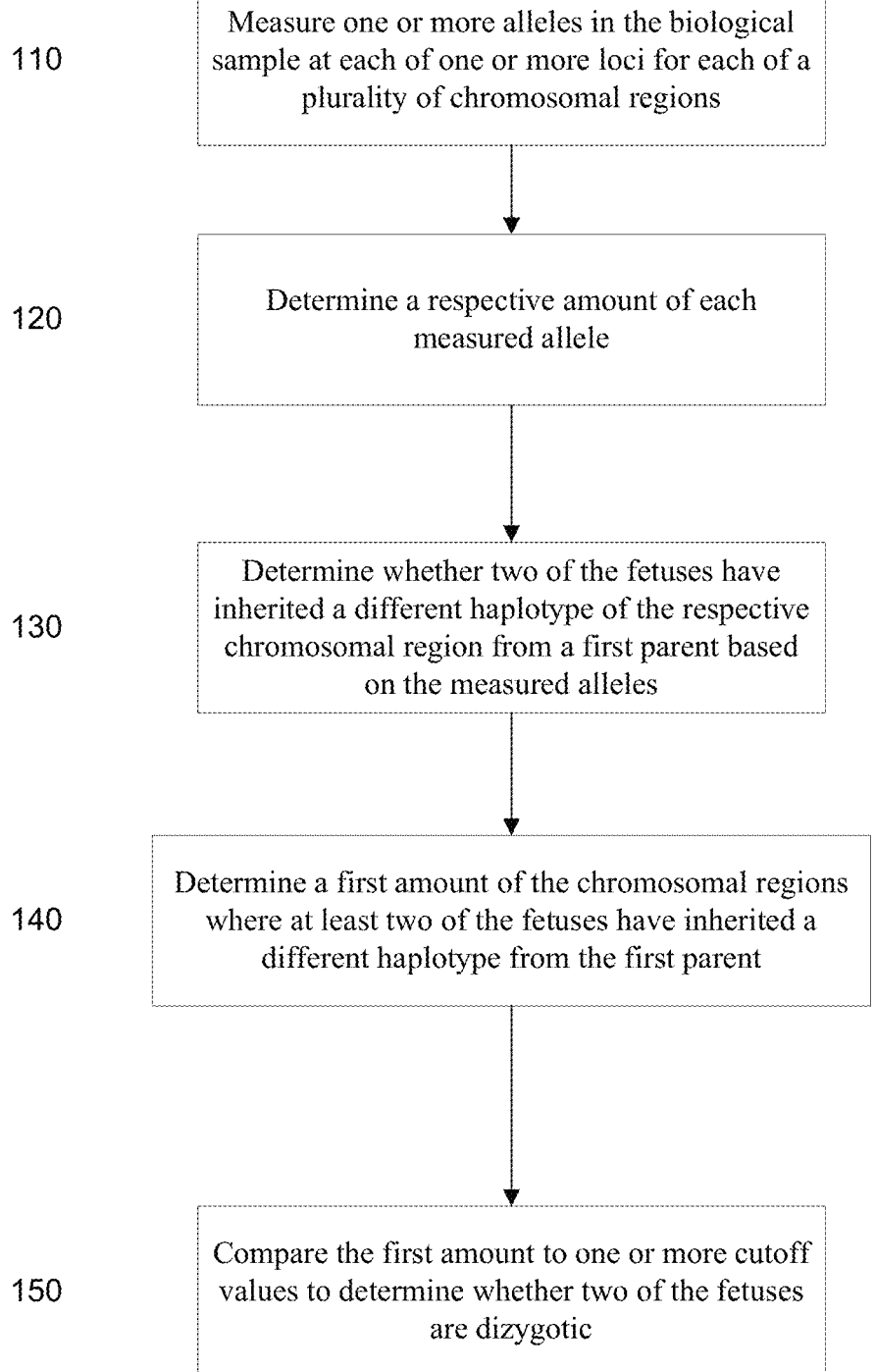
FIG. 1 is a flowchart illustrating a method 100 for analyzing a biological sample of a female pregnant with a plurality of fetuses to determine whether at least two fetuses of the pregnant female are dizygotic according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweath, ascitic fluid, bile, urine, serum, pancreatic juice, stool and cervical smear samples The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer M A et al., *Nucleic Acid Res* 1991; 19:5081; Ohtsuka E et al., *J Biol Chem* 1985; 260:2605-2608; and Rossolini G M et al., *Mol Cell Probes* 1994; 8:91-98). The term nucleic acid is used interchangeably with gene, cDNA, mRNA, small non-coding RNA, micro RNA (miRNA), Piwi-interacting RNA, and short hairpin RNA (shRNA) encoded by a gene or locus.

The term "gene" means the segment of DNA involved in producing a polypeptide chain or transcribed RNA product. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis, ligation, hybridization or degradation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, chamber in a PCR array, a droplet in an emulsion, a particle, a nanopore or an area on a surface.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" is a location or address of any length of nucleotides (or base pairs) which has a variation across genomes. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of an organism typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. The presence or absence of a sequence (e.g. a gene) is also considered to be a type of allelic variation, as a locus can include the sequence or not include the sequence. Such an absence of a sequence (e.g. the RHD gene) can be identified, for example, by the junction of the sequences that normally come before and after the deleted sequence. As used herein, the term "polymorphism" refers to any inter-individual variation in the human genome, regardless of its frequency. Examples of such variations include, but are not limited to, single nucleotide polymorphisms, simple tandem repeat polymorphisms, insertion-deletion polymorphisms, mutations (which may be disease causing) and copy number variations.

The term "haplotype" as used herein refers to a combination of alleles at multiple loci that are transmitted together on the same chromosome or chromosomal region. A haplotype may refer to as few as one pair of loci or to a chromosomal region, or to an entire chromosome. A "chromosomal region" refers to a plurality of nucleotide positions for a particular chromosome. The chromosomal region may be an entire chromosome or a smaller subsection. In a normal person, a chromosomal region will have two haplotypes, one for each copy of the chromosome that the region is within. The two haplotypes may be the same or different in the chromosomal region.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

The term "sequenced tag" refers to a sequence obtained from all or part of a nucleic acid molecule, e.g., a DNA fragment. In one embodiment, just one end of the fragment is sequenced, e.g., about 30 bp. The sequenced tag can then be aligned to a reference genome. Alternatively, both ends of the fragment can be sequenced to generate two sequenced tags, which can provide greater accuracy in the alignment and also provide a length of the fragment. In yet another embodiment, a linear DNA fragment can be circularized, e.g., by ligation, and the part spanning the ligation site can be sequenced.

The term "universal sequencing" refers to sequencing where adapters are added to the end of a fragment, and the primers for sequencing attached to the adapters. Thus, any fragment can be sequenced with the same primer, and thus the sequencing can be random.

The term "classification" as used herein refers to any number(s) or other characters(s) (including words) that are associated with a particular property of a sample. For example, a "+" symbol could signify that a sample is classified as having deletions or amplifications. The term "cutoff" and "threshold" refer a predetermined number used in an operation. For example, a cutoff size can refer to a size above which fragments are excluded. A threshold value may be a value above or below which a particular classification applies. Either of these terms can be used in either of these contexts.

The term "histogram" refers to a data structure storing a count of a number of data points within a specified range. For example, the number of chromosomal regions exhibiting a parameter (e.g. fetal DNA percentage) at a set of values.

The term "optimal" refers to any value that is determined to be numerically better than one or more other values. For example, an optimal value is not necessarily the best possible value, but may simply satisfy a criteria (e.g. a change in a cost function from a previous value is within tolerance).

DETAILED DESCRIPTION

Fetal DNA has been shown to be present in the plasma and serum of pregnant women (Lo et al. *Lancet* 1997; 350: 485-487; and U.S. Pat. No. 6,258,540). The analysis of fetal DNA in maternal plasma or serum has the advantages that it is relatively noninvasive, requiring just a sample of the mother's blood. Compared with conventional noninvasive methods for prenatal screening, e.g., ultrasound scanning, testing of fetal DNA in maternal plasma or serum would allow the direct assessment of the fetal genetic information. Here, we illustrate the principle of how DNA in maternal plasma or serum (or other biological sample) can be analyzed to differentiate if a pregnant woman is carrying monozygotic or dizygotic fetuses (e.g. a pair of monozygotic or dizygotic twins).

First, an analysis across multiple chromosomal regions to determine a level of difference between the fetal genomes, which is used to perform a classification regarding the zygosity of the fetuses. Next, we discuss specific examples of analyzing a particular chromosomal region to determine if the fetuses differ genetically in the region (e.g. if twins each has inherited a different paternal haplotype) when two different paternal haplotypes are known at a plurality of loci, and the mother is homozygous at these loci (an example where the mother is heterozygous and the father is homozygous is also discussed). Other examples when genotype information of both parents is known are also described, e.g., when three or more different alleles are at a particular locus. Then, a technique of comparing and/or identifying variations in a measure of an apparent fetal DNA concentration, or variances of other parameters across regions, is described. Such techniques may use explicit maternal genotype information, or deduce the maternal genotype via measurement of a biological sample containing fetal and maternal DNA, for example, plasma of a pregnant woman. The deductive technique for multi-fetus pregnancies is also explained.

I. Determining Zygosity Using Different Chromosomal Regions

Monozygotic fetuses are genetically identical, while dizygotic fetuses are genetically different. The degree of genetic difference would be similar to other siblings born to the same parents at other pregnancies. However, due to statistical chance, dizygotic fetuses may share the same genetic sequences at parts of the genome.

A fetus normally has two haplotypes (which may or may not be the same) for a particular chromosomal region, one haplotype for each of the two copies of the chromosome. If the fetuses are monozygotic, the fetuses would have the same two haplotypes in the chromosomal region. Also, dizygotic fetuses may have the same pair of haplotypes for a given chromosomal region due to statistical chance. Embodiments can analyze a plurality of chromosomal regions to detect whether the fetuses have inherited different haplotypes, and then a percentage (or other parameter) of regions that differ is used to determine whether the fetuses are monozygotic or dizygotic. A specified number of chromosomal regions may be analyzed to obtain a desired statistical significance.

A. Method

FIG. 1 is a flowchart illustrating a method 100 for analyzing a biological sample of a female pregnant with a plurality of fetuses to determine whether at least two fetuses of the pregnant female are dizygotic according to embodiments of the present invention. The biological sample includes fetal and maternal DNA. For example, plasma from a pregnant woman may be used. Method 100 may be implemented using a computer system, as can any of the methods described herein.

In step 110, for each of a plurality of chromosomal regions, one or more alleles in the biological sample are measured at each of one or more loci in the respective chromosomal region. The DNA in the biological sample may be analyzed by various techniques, including quantitative polymerase chain region (PCR), digital PCR, sequencing (e.g. Sanger sequencing and massively parallel sequencing), ligation, hybridization and mass spectrometry (such as the Sequenom MassARRAY platform) to measure particular alleles at the loci. For sequencing, an enriching step may be performed before the sequencing to increase the percentage of DNA fragments from a particular set of chromosomal regions. In one embodiment, such an enrichment step can be performed using solution phase (e.g. using the Agilent SureSelect platform) or solid phase (e.g. using the Roche NimbleGen platform) hybridization. The measuring step itself may be accomplished using data obtained from any one or more of the above techniques. For example, a sequenced tag can be aligned to a reference genome to identify the location and the allele of the corresponding DNA fragment from which the sequenced tag was obtained. One method that can be used for analyzing the DNA in the biological sample is a technique called Digital Analysis of Selection Region (DANSR), which involves the steps of hybridization, ligation, amplification and massively parallel sequencing (Sparks A B et al. *Am J Obstet Gynecol* 2012; doi: 10.1016/j.ajog.2012.01.030).

Examples of massively parallel sequencing platforms that can be used include the Illumina Genome Analyzer platform, the Life Technologies SOLiD, Ion Torrent and Ion Proton systems, the Roche 454 system, the single molecule sequencing system from Helicos, Pacific Biosciences, or a system based on nanopores (such as that from Oxford Nanopore Technologies). In another embodiment, targeted sequencing is performed, in which selected genomic regions (e.g. those containing SNPs or other types of variations such as microsatellite polymorphisms) are captured or amplified, and then massively parallel sequencing is carried out preferentially for such captured or amplified regions. In one embodiment, targeted sequencing is carried out using the Agilent SureSelect system (Liao G J et al. *Clin Chem* 2011; 57: 92-101). Targeted sequencing may also be carried out using the Roche NimbleGen system.

Digital PCR can be used for analyzing single DNA molecules in maternal plasma (Vogelstein B and Kinzler K W. *Proc Natl Acad Sci USA* 1999; 96: 9236-9241; Lo Y M D et al. *Proc Natl Acad Sci USA* 2007; 104: 13116-13121). Digital PCR can be carried out using a number of platforms, including but not limited to microfluidics (Lun F M F et al. *Clin Chem* 2008; 54: 1664-1672), emulsion PCR (Dressman D et al. *Proc Natl Acad Sci USA* 2003; 100: 8817-8822), including the RainDance platform (Kiss M M et al. *Anal Chem* 2008; 80: 8975-8981).

In step 120, a respective amount of each measured allele is determined. For example, DNA fragments in the sample can be sequenced (e.g. using universal sequencing) to obtain sequenced tags (which can be paired-end tags), and the sequenced tags can be aligned to a reference genome to identify the genomic location of the fragment. If genomes of the mother and/or fetus have variations at a locus, then different alleles will be measured for the locus. The respective amount of fragments corresponding to each allele at a locus can be tracked. The respective amount of a particular allele at a particular locus can be measured in various ways, such as by the number or proportion of fragments, the ratio between the different alleles at the same polymorphic site, the signal intensity on a microarray hybridization, the threshold cycle or difference in threshold cycles in a real-time PCR, the proportion or number of reactions positive for an allele as detected by digital PCR, and the peak height in a mass spectrometry analysis.

In step 130, for each of a plurality of chromosomal regions, it is determined whether two of the fetuses have inherited a different haplotype of the respective chromosomal region from a first parent based on the respective amounts of the measured alleles. If one fetus inherits a first haplotype and another fetus inherits a different haplotype, then this is an indication of dizygosity. If there are more than two fetuses, one pair may have inherited the same haplotype and a different pair may have inherited a different haplotype. In one embodiment, the inheritance of a different haplotype may be inferred from the measured data of the alleles at the one or more loci. For example, a deductive method may be used to identify a difference in the genomes of the fetuses, as is described below.

In another embodiment, genotype information from one or more of the parents may be known. Such information can allow measurements from only one locus to be used to determine where a different haplotype has been inherited from the first parent. For example, if there are three different genotypes in the parents at a first locus, then one can make the determination using just the first locus. However, if there are only two genotypes at a locus, then measurements at another locus may be needed. Some examples are provided below.

If a plurality of loci are used for a chromosomal region, the data from the loci may be combined in various ways. For instance, if an allele is known to be associated with a particular haplotype, then a count of the number of fragments with a particular allele at a particular locus effectively becomes a count of the number of fragments for a particular haplotype. For example, one can determine a number of fragments corresponding to a first haplotype of the first parent (e.g. the father) by summing the counts for the fragments having the allele and locus of the first haplotype. Alternatively, a determination can be made independent for each locus, and the determinations for each locus can be compared for consistency.

In step 140, a first amount of the chromosomal regions where at least two of the fetuses have inherited a different haplotype from the first parent is determined. The first amount may simply be the number of chromosomal regions that have been identified as having differences between the fetuses. As another example, the first amount may be a percentage of chromosomal regions identified as having differences between the fetuses.

In step 150, the first amount is compared to one or more cutoff values to determine whether the two fetuses are monozygotic or dizygotic. For example, the first amount may be a percentage (or other proportion), such as 10% and this amount may be compared to a cutoff value, where above 5% is classified as dizygotic. The cutoff value can be determined based on a desired accuracy, the accuracy of determination in step 130, the number of chromosomal regions used, and the linkage disequilibrium of the different chromosomal regions in the population and the probability of recombinations between the different chromosomal regions analyzed, which are described in the next section. In one aspect, if there are more than two fetuses, the determination may just be that one pair is dizygotic, thus leaving open the possibility that the other pair is monozygotic.

B. Statistical Analysis for Haplotype Detection

As mentioned above, the inheritance of both haplotypes (i.e. when different) of a chromosomal region from a parent indicate that the pair of twins are dizygotic instead of monozygotic. For example, the detection of both paternal haplotypes at a first locus of a chromosomal region would indicate that the pair of twins are dizygotic. However, there are several possible explanations for detecting only one paternal haplotype for a chromosomal region in a maternal plasma sample.

First, the two fetuses can have inherited, just by chance, the same paternal haplotype in the chromosomal region from the father. When they are a pair of monozygotic twins, they would always inherit the same paternal haplotypes from the father across the whole genome. However, even if they are dizygotic twins, there is a 50% chance that they would inherit the same paternal haplotype from the father for any specific region. However, it would be extremely unlikely that the pair of dizygotic twins would inherit identical paternal haplotypes across the whole genome.

In another scenario, the two dizygotic twin fetuses may have inherited different paternal haplotypes but only one paternal haplotype is detected in a particular analysis due to inadequate sampling. The probabilities of these various scenarios occurring are dependent on the fractional fetal DNA concentration in the maternal plasma sample and the number of maternal plasma DNA molecules analyzed for the particular chromosomal region. Below, we provide a calculation on how many molecules corresponding to a chromosomal region and how many chromosomal regions may be used to arrive at a robust classification with sufficient statistical power to minimize the chance of false haplotype interpretation due to inadequate sampling.

The number of molecules corresponding to a particular chromosomal region that needs to be analyzed can be determined in the following way. When a paternal haplotype is present in the maternal plasma, the probability of detecting it in a particular maternal plasma DNA sample is dependent on the fractional concentration of fetal DNA carrying that paternal haplotype and the total number of molecules analyzed, and is governed by the Poisson distribution.

Table 1 shows the number of molecules corresponding to the chromosomal region of interest that need to be analyzed so that the probability of having a paternal haplotype present in a maternal plasma but not detected in the particular sample is less than 1%. The figures are calculated based on the following formula: $0.01 > \exp(-N \times f/2)$, where $N$ is the number of molecules needed to be analyzed; $f$ is the fractional fetal DNA concentration contributed by a single twin fetus; and exp is the exponential function. The number of molecules is the number of DNA fragments at any of the loci used to analyze the chromosomal region. The number of molecules that need to be analyzed to achieve the desired certainty of detecting the paternal haplotype can be attained by measuring one locus in the chromosomal region up to the numbers listed in Table 1. Alternatively, if several loci in the same chromosomal region are analyzed, the number of molecules needed to be analyzed per locus could be reduced to an extent that as long as the number of loci multiplied by the average number of molecules analyzed per locus reaches the molecule numbers listed in Table 1.

TABLE 1

Number of DNA fragments to be analyzed to achieve less than 1% probability of detecting a paternal haplotype for various fetal DNA concentrations.

| Fractional fetal DNA concentration contributed by a single twin fetus (%) | No. of molecules need to be analyzed |
| --- | --- |
| 20 | 46 |
| 15 | 61 |
| 10 | 92 |
| 8 | 115 |
| 6 | 154 |
| 4 | 230 |
| 2 | 461 |

The number of chromosomal regions needed to be analyzed can also be determined. Assuming that the chromosomal regions are not in linkage disequilibrium, the chance of the two dizygotic twins inheriting different paternal haplotypes would be 50% for each of the different chromosomal regions. If the number of chromosomal regions is n, then the probability of a pair of dizygotic twins having inherited an identical paternal haplotype for each of these n chromosomal regions would be $2^{-n}$. Therefore, when seven independent chromosomal regions are analyzed, the chance of a pair of dizygotic twins having inherited identical paternal haplotypes for each of the 7 regions would be less than 1%. In this case, the cutoff in step 140 can be 14%, where one region showing different inherited haplotypes out of seven would provide a classification of dizygosity. An absolute value of one region may also be used. If a large number of regions (e.g. 50 or 100) are used, one or more regions indicating different inherited haplotypes may be allowed while still providing a classification of monozygosity.

II. Using Parental Genotypes to Identify Fetal Haplotypes

As mentioned above, the parental genotypes at one or more loci of a chromosomal region may be used to help determine whether two fetuses have inherited different haplotypes from a parent. For example, the detection of two different paternal haplotypes corresponding to the same genomic region in a maternal plasma sample which is taken from a woman having a twin pregnancy can be used. Although the analysis below focuses on examples based on the detection of two different paternal haplotypes, variations of the technique may also be applied to two different maternal haplotypes.

a. SNP Analysis at Two Loci

FIG. 2A shows an example for determining the zygosity when one knows the genotypes for the mother at two different loci and the haplotypes of the father for a given chromosomal region. This embodiment focuses on SNP loci that the pregnant mother of the twins is homozygous and the father of the twins is heterozygous. In the example shown in FIG. 2A, the mother is homozygous at the SNP loci 1 and 2 with genotypes AA and TT, respectively. The father is heterozygous at the SNP loci 1 and 2 with genotypes AC and GT, respectively.

Assuming that loci 1 and 2 are close, i.e. recombination is unlikely (e.g. probability of recombination occurring between the two loci <0.1%) to occur between the two loci, the alleles at the two loci would be inherited by the fetus together and form a haplotype. As the mother is homozygous for both locus 1 and locus 2, she has two identical haplotypes. We define these two identical maternal haplotypes as Hap I and Hap II. On the other hand, the father has two different haplotypes and we define them as Hap III and IV as illustrated in FIG. 2A.

When a pregnant woman is carrying a pair of monozygotic twins, the genetic makeup of the two fetuses would be identical. In other words, only one of the two paternal haplotypes would be inherited by these two twin fetuses. In the illustrated example, both fetuses inherit Hap III from the father.

When a maternal plasma sample is analyzed, only allele A would be detected for locus 1 because the mother and both fetuses are homozygous for allele A. The absence of the C allele in maternal plasma would indicate that none of the fetuses has inherited Hap IV from the father when the number of molecules corresponding to locus 1 being analyzed is sufficiently large. The number of molecules required to be analyzed would be dependent on the fractional fetal DNA concentration in the maternal plasma DNA sample and the statistical power required for ruling out the presence of the C allele in the maternal plasma sample, e.g. as shown in Table 1.

On the other hand, both the T and G alleles would be detected in the maternal plasma sample for locus 2. As the mother is homozygous for the T allele, this indicates that at least one of the fetuses inherits Hap III from the father. Taken together the information from locus 1 and locus 2, both fetuses would have inherited Hap III from the father.

In the situation of dizygotic twins, the two twin fetuses could have inherited different haplotypes from the father. In the example of FIG. 2A, twin 1 has inherited Hap III and twin 2 has inherited Hap IV from the father. Therefore, in the maternal plasma, both the A and C alleles could be detected for locus 1 and both the G and T alleles could be detected for locus 2. The detection of an allele at a locus can be quantified to ensure that the detection is not spurious (e.g. only one or two alleles of a particular type are measured due to analytical errors). For example, the number of alleles of a particular type can be measured and compared to a threshold, which ensures that a statistically significant amount of the particular allele have been measured. The cutoff can vary based on the number of measurements made for a sample (e.g. number of alleles measured for a particular locus). For instance, if one measured 1,000 alleles for a locus, then the threshold may be larger than if only 100 alleles were measured at the locus. Thus, an allele may be considered detected if a measured amount is above a threshold.

These findings indicate that both paternal Hap III and Hap IV are present in the maternal plasma. As each fetus can only inherit one haplotype from the father, these findings further indicate that the two fetuses have inherited different haplotypes from the father and, hence, they are genetically different. Therefore, the two fetuses would be identified as having inherited different haplotypes for the chromosomal region that includes loci 1 and 2, and as such the two fetuses may be determined to be a pair of dizygotic twins, e.g., just using this chromosomal region or in combination with data from other chromosomal regions.

Accordingly, when the first parent is the father, two haplotypes of the first parent can be determined at a plurality of loci for a first chromosomal region. For example, Hap III and Hap IV can be determined for a particular chromosomal region. Determining that two of the fetuses have inherited a different haplotype of the first chromosomal region from the first parent can proceed as follows. A first locus and a second locus (e.g., locus 1 and locus 2) can be identified in the first chromosomal region at which the first parent is heterozygous and the paternally unique allele (i.e. not represented in the maternal genome) at locus 1 and locus 2 are not present on the same paternal haplotype.

A statistically significant amount of the first haplotype of the first parent at the first locus can be detected in the biological sample. As described above, this can be accomplished when the mother is homozygous for a first allele (A for locus 1) and the father is heterozygous with the second allele on the first haplotype, which is Hap IV for locus 1. The number of DNA fragments with the second allele (C for locus 1) can be detected and compared to a cutoff (threshold) value to determine if a statistically significant amount of the first haplotype has been detected. The number of DNA fragments containing the second allele (an example of a measured amount of the second allele) can be used by itself (e.g. the cutoff can be an absolute number) or normalized (e.g., the cutoff can be a proportion).

A statistically significant amount of a second haplotype of the first parent at the second locus can then be detected in the biological sample. As described above, this can be accomplished when the mother is homozygous for a third allele (T for locus 2) and the father is heterozygous with the fourth allele on the second haplotype, which is Hap III for locus 2. The number of DNA fragments with the fourth allele (G for locus 1) can be detected and compared to a cutoff (threshold) value to determine if a statistically significant amount of the first haplotype has been detected. Note that the third and fourth alleles could be A and C again, but with C on Hap III.

Accordingly, an embodiment can determine if a first haplotype of a first parent is inherited by any of the fetuses for a chromosomal region. If the first haplotype has been inherited, then it is determined if a second haplotype of the first parent is inherited by any of the fetuses for the chromosomal region. If the second haplotype has also been inherited for the chromosomal region, then the fetuses are classified as dizygotic. The above discussion provided an example where the first parent was the father, and now an example is provided where the first parent is the mother.

Figure 2B:
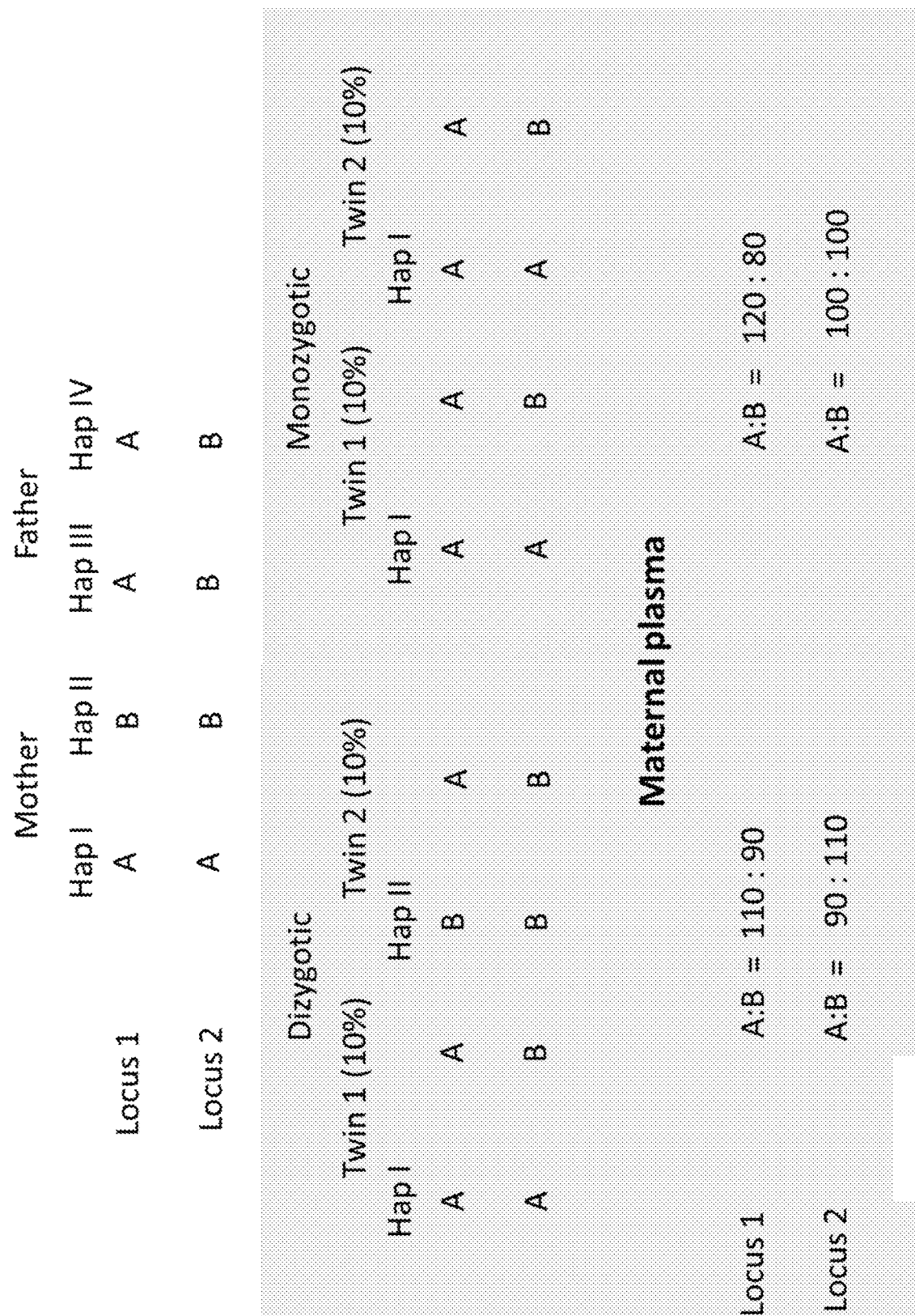

Quantitative analysis of the two maternal haplotypes can also be used to determine if the two fetuses are monozygotic or dizygotic. FIG. 2B shows an example for determining the zygosity when one knows the genotypes for the father at two different loci and the haplotypes of the mother for a given chromosomal region. In the scenario where the two fetuses are monozygotic, the two fetuses would inherit the same maternal haplotype for all chromosomal regions. The haplotype inherited by the fetuses would be present in higher concentrations in maternal plasma. The difference in the concentrations of the two maternal haplotypes is proportional to the fractional concentration of fetal DNA in the maternal plasma. This is shown in FIG. 2B for locus 1 where the A allele occurs more often than the B allele by a difference proportional to the 20% fetal DNA concentration. Then for locus 2, equal amounts of allele A and allele B are present since the father is homozygous for allele B. If the fetuses contribute unequal percentages of fetal DNA, the ratios of allele A to B for locus 1 one would depend on the total fetal DNA percentage (i.e. a sum of the individual fetal DNA percentages). If the fetuses contribute unequal percentages of fetal DNA, the ratios of allele A to B for locus 1 would positively correlate to the total fractional fetal DNA concentration (i.e. a sum of the individual fractional fetal DNA concentrations or fetal DNA percentages). In this invention, the terms fractional fetal DNA concentrations and fetal DNA percentages are used interchangeably.

On the other hand, when the two fetuses are dizygotic, the two fetuses might inherit different maternal haplotypes at any chromosomal region. When the two fetuses inherit different maternal haplotypes at a particular chromosomal region, the two maternal haplotypes would be present in equal amounts in the maternal plasma. Therefore, the presence of equal representation of the two maternal haplotypes at one or more chromosomal regions could potentially be used to indicate the presence of a pair of dizygotic twins. This equal representation manifests itself as a same difference between alleles A and B for both locus 1 and locus 2, but the overrepresented allele is different. The fact that the overrepresented allele is from a different haplotype can be used to identify that the fetus have identified different haplotypes of the mother. Note that the degree of overrepresentation is half (10% as shown) of the total fetal DNA percentage. Such a phenomenon is discussed in more detail later. If the fetuses contribute unequal percentages of fetal DNA, the ratio of allele A to B for locus 1 would depend on the fetal DNA percentage contributed by twin 1; and the ratio of allele A to B for locus 2 would depend on the fetal DNA percentage contributed by twin 2. Note that the alleles on Hap I do not have to be the same for both loci.

Accordingly, a method can detect different haplotypes of the mother being detected when the maternal haplotypes are known at a first locus and a second locus. As in FIG. 2B, the father is homozygous at the first locus for a first allele (A as shown), and the mother is heterozygous for the first allele and a second allele (B as shown) at the first locus. The first allele is on the first haplotype (Hap I as shown) and the second allele is on the second haplotype (Hap II as shown) of the mother. Detecting the first haplotype of the first parent at the first locus can include determining that the respective amount of the first allele measured at the first locus is greater than the respective amount of the second allele measured at the second locus by a statistically significant amount. This is shown by the ratio of 110:90. In one implementation, a cutoff value can be used to ensure that the difference between the values is statistically significant.

For the second locus, the father is homozygous at the second locus for a fourth allele (B as shown, but can be any allele including A), and the mother is heterozygous for the third allele (A as shown) and a fourth allele (B as shown) at the second locus. The third allele is on the first haplotype and the fourth allele is on the second haplotype of the mother. Detecting in the biological sample the second haplotype of the first parent at the second locus can include determining that the respective amount of the fourth allele measured at the second locus is greater than the respective amount of the third allele measured at the second locus by a statistically significant amount.

b. Analysis for Other Types of Polymorphisms

The example above involved different nucleotides at a locus being used to determine whether different haplotypes have been inherited from a first parent for a chromosomal region. However, polymorphisms other than SNPs can also be used as markers for different paternal haplotypes. Examples of other types of polymorphisms include but are not limited to microsatellites, restriction fragment length polymorphisms, insertion/deletion polymorphisms, and copy number variations (CNV). Such other polymorphisms can result in the configuration of FIGS. 2A and 2B, but where the first allele and the second allele result from one of these other polymorphisms. For any polymorphism, more than two alleles can also be present. Below is an example.

FIG. 3 also shows an example of microsatellite analysis where a locus has four different alleles. Microsatellites are polymorphic regions in the genome comprising of a variable number of short tandem repeats (STRs). In this example, the mother has two different alleles for this microsatellite region, namely Allele I and Allele II, comprising of 4 and 7 repeats, respectively. The father also has two alleles, namely Allele III and Allele IV, comprising of 5 and 8 repeats, respectively. Thus, the locus actually has four different alleles among the parents.

As the genetic makeup of a pair of monozygotic twins would be identical, they would have inherited the same paternal allele. As a result, only one paternal allele can be detected in the maternal plasma. In this example, only the paternal Allele III with 5 repeats, together with the maternal allele I with 4 repeats could be detected in the maternal plasma sample. When multiple loci are analyzed for a given chromosomal region and only one paternal allele could be detected in the maternal plasma sample for each of the loci, then one would statistically determine the probability of the twins being monozygotic, as described above.

On the other hand, when the pair of twins are dizygotic, the two twin fetuses can inherit different paternal alleles. As illustrated in FIG. 3, one of the dizygotic twins has inherited Allele III from the father and the other has inherited Allele IV. As a result both paternal alleles could be detected in the maternal plasma sample, e.g., via detection methods described above. In other words, if both paternal alleles can be simultaneously detected in a maternal plasma sample, the twin fetuses would be dizygotic, unless the fetuses have a chromosomal aberration (e.g. the fetuses are trisomic at the locus). A similar analysis can be performed if the mother is homozygous at the locus, e.g., for a repeat of 4 (or any other allele of a polymorphism).

Thus, in the situation where the polymorphism has three or more alleles, one could detect a dizygotic twin pregnancy if two paternally-inherited alleles, both of which are absent in the genome of the pregnant woman, are detected in maternal plasma. In one embodiment, such a genotype pattern in maternal plasma would be supported by ultrasound evidence of the presence of a twin pregnancy. In the absence of such ultrasonic evidence of a twin pregnancy, such a plasma genotype pattern would indicate the presence of a trisomic fetus (Ghanta S et al. *PLoS ONE* 2010; 5: e13184).

III. Identifying Variations in Genomic Regions

The previous section described example techniques for determining whether a different haplotype of a chromosomal region was inherited from a first parent. In such examples, parental genotype information was known for both parents, and used in the analysis. In the following description, the genotype of the parents is not needed, although it may be used. For example, a fetal DNA concentration (or other parameter) will show different values at various loci for dizygotic fetuses.

A. General Method

FIG. 4 is a flowchart illustrating a method 400 for analyzing a biological sample of a female pregnant with a plurality of fetuses to determine whether at least two fetuses of a pregnant female are genetically different for a first chromosomal region according to embodiments of the present invention. As with other methods, the biological sample includes fetal and maternal DNA. Method 400 may be used to perform step 130 of method 100.

In step 410, the genotype of the pregnant female is determined at each of one or more first loci within a first chromosomal region. The first loci are such that the pregnant female is homozygous at each of the one or more first loci or are heterozygous at each of the one or more first loci. Accordingly, each of the first loci are of the same category (i.e. homozygous or heterozygous) for the maternal genotype. The genotypes can be determined in various ways. For example, the buffy coat or cell pellet layer from whole blood of the pregnant female can be analyzed, where predominantly only maternal DNA is present or other maternal-only sample. Standard genotype techniques may be used. As another example, the genotypes may be deduced from an analysis of the biological sample that includes fetal and maternal DNA (such a technique is described in more detail below).

Each of the first loci exhibits a primary allele and a secondary allele, i.e. the biological sample contains the primary allele and the secondary allele for each of the loci. When the mother is homozygous at the first loci, the secondary allele is contributed by at least one fetus. In such a situation, each locus would have a primary allele and a secondary allele, where the primary allele is more abundant than the secondary allele. When the mother is heterozygous and at least one fetus is homozygous, the primary allele is also more abundant than the secondary allele. However, when the mother is heterozygous and all of the fetuses are also heterozygous (for the same alleles), neither the primary allele nor the secondary allele is more abundant. The fact that the loci each have a primary allele and a secondary allele can be determined in various ways, e.g., by detecting the alleles (see step 420) or by knowledge (deductive or explicit) of the parental genotypes.

In step 420, a respective primary allele and/or a respective secondary allele can be detected in the biological sample at each of the first loci. For embodiments where only the primary alleles or only the secondary alleles are detected, the knowledge of the existence of the other allele can be obtained through some information about the parental genotypes. For example, if secondary allele B is detected and the mother is known to be homozygous for primary allele A at a locus, then it can be determined that the biological sample has two alleles at the locus. Such an example is the case where the mother is RhD-negative (and thus homozygous for the allele represented by the absence of the RHD gene), and the RHD gene is detected in the biological sample. Both alleles at each locus may also be detected.

If a primary and secondary allele are known to exist at a locus, then the fetal genotypes can be identified to effectively be of a similar category. For example, if the mother is homozygous for allele A at one of the loci, then allele A would be the primary allele. And, since a secondary allele B would be detected, it is known that at least one of the fetuses is heterozygous. Thus, all of the first loci would be of a category $AA_{AB}$, where the subscript indicates that at least one of the fetuses is heterozygous. For an example where the mother is heterozygous AB, and at least one of the fetuses is homozygous AA, then B again would be the secondary allele and A would be the primary allele. In this case, all of the first loci would be of a category $AB_{AA}$, where the subscript indicates that at least one of the fetuses is homozygous.

In step 430, a first amount of the one or more primary alleles and/or a second amount of the one or more secondary alleles is measured in the biological sample at the one or more loci. Each locus can have a different primary allele, but the amounts of each primary allele can be combined (e.g., summed) to obtain the first amount. The same can be done for the second amount. In one embodiment, only the first amount is determined. In another embodiment, only the second amount is determined. In yet another embodiment, both the first and second amounts are determined. Steps 420 and 430 may be accomplished at the same time, and thus effectively be the same step.

In step 440, a normalized parameter for the first amount or the second amount is obtained. In one embodiment, the normalized parameter is obtained by calculating a fractional parameter value (e.g., a fractional fetal DNA concentration) for the first region, where the fraction is the first amount relative to the second amount. In one aspect, the fractional fetal DNA concentration is an apparent value since it may differ from the actual fetal DNA concentration when two fetuses are genetically different in the first chromosomal region (e.g. only one is heterozygous). In another embodiment, the normalized parameter is obtained in a calibrated fashion, i.e., in a same manner or in a correlated manner as an expected value, which is described below. The correlated manner may be any procedure that reproducibly provides a value that is of a fixed difference or ratio (e.g., one technique regularly provides 1.2 times the value of another technique, or there is a conversion curve for translating results obtained from one technique to an expected value for the other technique. Thus, the normalized parameter may simply be the first amount (or second amount) if it is obtained in a calibrated fashion.

The normalized parameter can also be determined by calculating a third amount of one or more other sequences (e.g. an allele or a homozygous sequence) from one or more loci within another chromosomal region, and then use the third amount to normalize the first amount or the second amount. Such a normalization (as well as other types of normalization) can allow a comparison of amounts calculated for other regions using different techniques or uncalibrated techniques. For calibrated techniques either the first amount or the second amount can be compared to measurements from other regions. Using either the first amount or the second amount can convey the same information.

In step 450, the normalized parameter is compared to a cutoff value to determine if the normalized parameter is statistically different from an expected value if the fetuses are genetically the same for the first chromosomal region. For example, the number of secondary alleles will be different if only one of the fetuses is heterozygous compared to the number when all fetuses are heterozygous or homozygous. The expected value (e.g. a fetal DNA concentration) can be obtained from measurements of the biological sample, e.g., from other chromosomal regions, quantifying the amount of chromosome Y sequences, or using one or more epigenetic markers, as described in more detail below. Other expected values can be derived from such measurements of fetal DNA concentration or measured directly, and thus the expected value is not limited to an expected fetal DNA concentration.

The cutoff value can be chosen based on a desired accuracy. For example, one may know that a standard deviation of a measurement of the expected value. Then, the cutoff can be chosen to be the expected value minus (or plus as the case may be) three times the standard deviation (SD). In this manner, an embodiment can determine that the difference (or deviation of a ratio from 1) of the normalized parameter from the expected value is statistically significant based on the relation to the cutoff value. In other embodiments, the cutoff may be 2.0, 2.5, 3.5, or 4 SDs.

In step 460, it is determined whether two fetuses of the pregnant female are dizygotic based on the comparison of the normalized parameter to the cutoff value. For example, it can be determined that two fetuses of the pregnant female are genetically different for the first chromosomal region when the normalized parameter is statistically different from the expected value. If the normalized parameter is not statistically different than the expected value, then the fetuses can be determined as being monozygotic. Such a determination of the chromosomal region can be combined with measurements from other chromosomal regions for the determination of zygosity, e.g., as described above for step 150. Alternatively, a determination of two fetuses not being identical for the first chromosomal region can provide a classification of dizygosity without measurements of other chromosomal regions.

B. Apparent Fractional Parameter (Fetal DNA Concentration)

Figure 5:
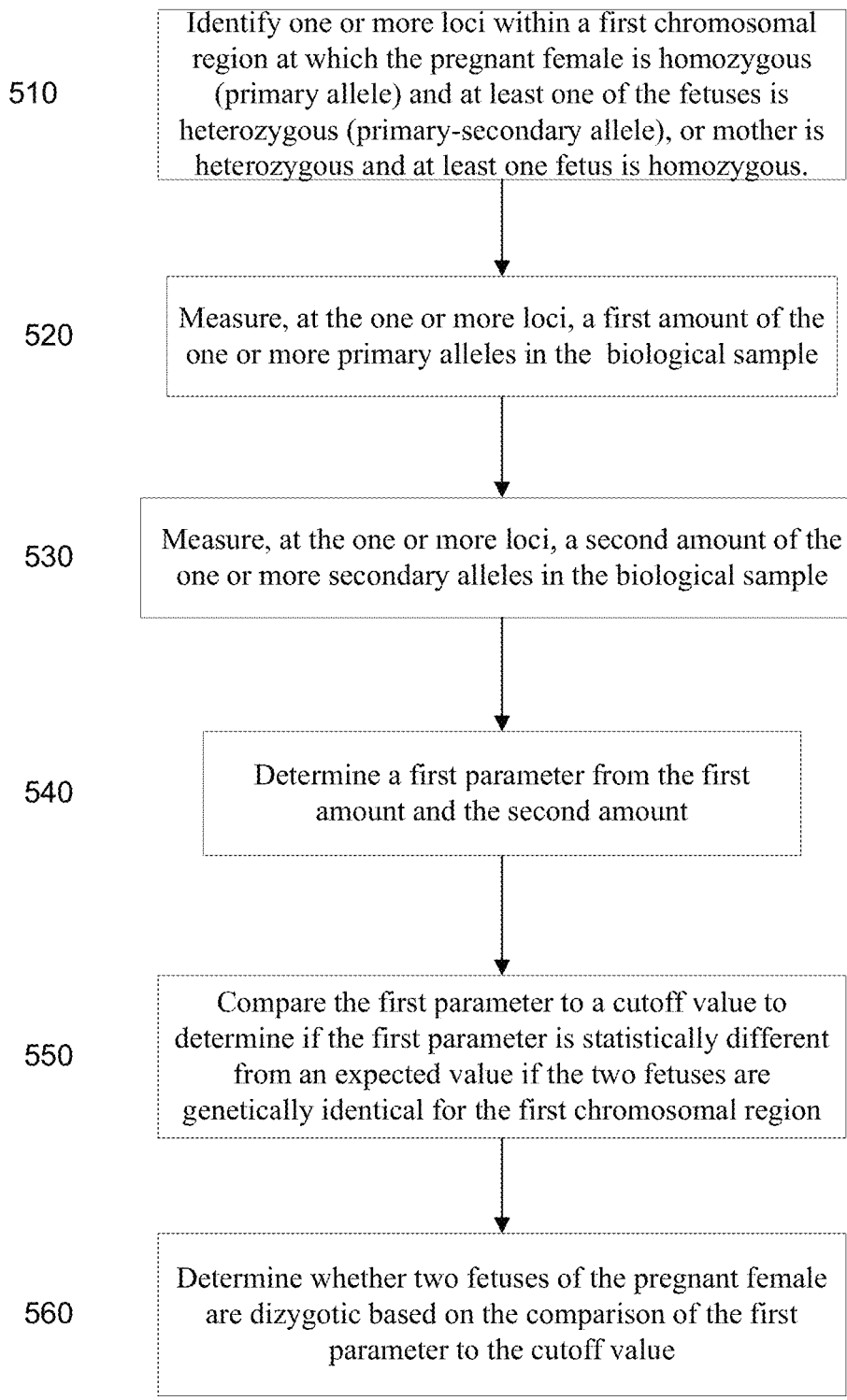
FIG. 5 is a flowchart illustrating a method 500 for determining whether at least two fetuses of a pregnant female are genetically different for a first chromosomal region from a first parent by determining an apparent fractional parameter (e.g., a fetal DNA concentration) for the first chromosomal region.

As mentioned above, the normalized parameter in step 440 can be a fractional value including the first amount and the second amount. FIG. 5 is a flowchart illustrating a method 500 for determining whether at least two fetuses of a pregnant female are genetically different for a first chromosomal region from a first parent by determining an apparent fractional parameter (e.g., a fetal DNA concentration) for the first chromosomal region. Method 500 analyzes a biological sample of a female pregnant with a plurality of fetuses, as in method 400. Although, method 500 is described for the situation where the mother is homozygous at the first loci, the method can equally be performed for loci where the mother is heterozygous.

In step 510, one or more loci within a first chromosomal region at which the pregnant female is homozygous and at least one of the fetuses is heterozygous is identified. In such a situation, each locus would have a primary allele and a secondary allele, where the primary allele is more abundant than the secondary allele. For example, if the mother is homozygous for allele A, then allele A would be the primary allele. Alternatively, one or more loci at which the pregnant female is heterozygous and at least one of the fetuses is homozygous can be identified, where the allele that is homozygous for the fetus would be the primary allele.

Such a locus can be identified by analyzing the alleles resulting from a measuring step, such as step 110. For example, a measurement of the alleles at a particular locus may show that a majority is allele A (primary allele), e.g., greater than 70%, and that only one other allele (e.g., T) is counted in a significant amount. Such a measurement can indicate that the mother is homozygous for allele A, and that at least one of the fetuses is heterozygous for allele T. Different cutoffs (e.g. a higher fraction of the secondary allele) can be used to determine if the mother is heterozygous and at least one fetus is homozygous. Various cutoff values for determining whether the locus satisfies the above conditions can be determined based on assumed or measured fetal DNA concentrations. U.S. patent application Ser. No. 12/940,993 describes such a technique in more detail for pregnancies with one fetus. A further section below provides a more complex procedure for obtaining genotype information for a locus in a multiple-fetus pregnancy.

In step 520, a first amount q of the one or more primary alleles are measured in the biological sample at the one or more loci. Each locus can have a different primary allele, but the amounts of each primary allele can be combined (e.g., summed) to obtain the first amount. In this manner, the depth of coverage of the analysis for the chromosomal region is essentially increased since multiple loci are used. For example, a limited amount of alleles may be measured for each locus, but once the loci are viewed in aggregate, a sufficient number of alleles may be measured to obtain statistical robustness. The loci within the chromosomal region can be chosen such that the chance of recombination between the loci is low, e.g., less than 1%.

In step 530, a second amount p of the one or more secondary alleles are measured in the biological sample at the one or more loci. In a similar manner, each locus can have a different secondary allele, but the amounts of each secondary allele can be combined (e.g., summed) to obtain the second amount. The secondary allele may arise from different haplotypes among the loci.

In step 540, a first parameter is determined from the first amount and the second amount. The first parameter provides a relative amount between the first amount and the second amount. For example, the first parameter may be a measure of the fractional fetal DNA concentration F computed as: $F=2p/(p+q)$. Other examples include any ratio of the two amounts, ratio of functions of the first amount, or functions of such ratios. Another example is a difference between the two amounts, which may be normalized.

In step 550, the first parameter is compared to a cutoff value to determine if the first parameter is statistically different from an expected value if the two fetuses are genetically the same in the first chromosomal region. For example, if both fetuses are heterozygous for the primary and secondary alleles at the loci in the first chromosomal region, then the first parameter should be equal to the total fetal DNA concentration when the formula above is used. However, if one of the fetuses is also homozygous at the loci, then the fetal DNA concentration will be less than the total fetal DNA concentration. The expected fetal DNA concentration can be obtained from measurements of the biological sample, e.g., from other chromosomal regions, measuring the amount of chromosome Y sequences if both fetuses are known to be males (for example by ultrasound scanning) or using one or more epigenetic markers, both of which are described in more detail below. Other expected values can be derived from such measurements of fetal DNA concentration or measured directly, and thus the expected value is not limited to an expected fetal DNA concentration.

In step 560, it is determined whether two fetuses of the pregnant female are dizygotic based on the comparison of the first parameter to the cutoff value. For example, it can be determined that two fetuses of the pregnant female are genetically non-identical in the first chromosomal region when the first parameter is statistically different from the expected value. If the normalized parameter is not statistically different from the expected value, then the fetuses can be determined as being monozygotic. When the first parameter is the fractional fetal DNA concentration, the first parameter may be an apparent fractional fetal DNA concentration, and not the actual fetal DNA concentration. The term apparent is used because the calculation of the fractional fetal DNA concentration may differ when two fetuses are dizygotic, and thus the calculated value is not the actual fractional fetal DNA concentration.

Accordingly, an apparent fractional fetal DNA concentration (F) in a maternal plasma sample can be determined at polymorphic loci (e.g. SNP loci) which are homozygous in the mother and heterozygous for at least one of the twins according to the formula:

$$F=2p/(p+q),$$

$$(x+a)^n = \Sigma_{k=0}^n \binom{n}{k} x^k a^{n-k}$$

where p is the count of the DNA molecules carrying the fetal-specific allele, and q is the count of the DNA molecules carrying the allele shared by the fetus and the mother. The SNP loci suitable for apparent fractional fetal DNA concentration analysis are those where two different alleles are detected for an individual SNP locus in the maternal plasma as described in the previous sections of this application. Such loci can be of the type where the mother is homozygous or heterozygous, but regions should be of the same type when compared.

For the calculation of the fractional fetal DNA concentration, the information from one SNP locus or multiple SNP loci can be used. The read counts from multiple SNP loci can be summed together. In other words, the SNP loci across the genome are divided into "groups". The loci of a group should preferably be in the same contiguous stretch of DNA. In one embodiment, such groups involve SNPs on the same chromosomal arm. In another embodiment, such groups involve SNPs within 1 kb, 5 kb or 10 kb stretch of DNA. The number of SNP loci within each group would be dependent on the desired precision of the measurement of the fractional fetal DNA concentration and the depth of coverage of each SNP locus (i.e. number of times each SNP locus is detected and quantified). In one aspect, the desired precision of the measurement of the fractional concentration would be the minimal precision that allows one to determine if two different groups of SNP loci have the same or at least two different apparent fractional fetal DNA concentrations.

With a higher depth of coverage of each SNP locus, the number of SNPs that is required for precisely measuring the fractional fetal DNA concentration can be reduced. In one embodiment, the depth of coverage for the SNP loci of interest can be increased by the targeted sequencing approach (Liao G J et al. *Clin Chem* 2011; 57:92-101). In this approach, the plasma DNA molecules are first hybridized to probes which are complementary to sequences in a region-of-interest and the captured molecules are subjected to massively parallel sequencing. The calculation on the number of molecules required will be discussed in a later section.

C. Using Amounts for Different Regions as Expected Value

As mentioned above, the expected value can be determined from an analysis of another chromosomal region. For example, a second parameter can be determined for a second chromosomal region (e.g., in a similar manner as described above), and such a value can be used as the expected value. In the case that all of the fetuses are heterozygous, for example A:T, at a locus for the second chromosomal region (for example when the mother is homozygous A:A and the father is known to be T:T), then the second parameter obtained from the two amounts of the two alleles can provide the expected value for the total fetal DNA concentration. Then, when the first parameter for the first region is statistically different from the expected value, as determined for the second region, the data suggest that only one fetus is heterozygous at a locus in the first chromosomal region and the fetuses are genetically different. Other techniques may be used to determine the expected value, as explained in the next section.

Parameters for other chromosomal regions can also be determined, and each can be used in multiple iterations of method 400. Various embodiments can group the determined parameters into clusters and determine if the clusters differ from each other, as will be described in more detail later. Such clusters can first be filtered to make sure that similar regions of the mother are being used, e.g., to ensure that the mother is homozygous at the regions whose parameter values are being clustered. Then, if two or more clusters of parameter values appear in the data, one can surmise that some regions are the same between the fetuses, but other regions differ, thereby indicating dizygosity. Accordingly, regional genomic variations in fetal DNA fractions in maternal plasma can reveal the zygosity of twin pregnancies. In the example below, an apparent fractional fetal DNA concentration analysis is used, but other parameters may also be used.

The determination of whether a pair of twins are monozygotic or dizygotic can be achieved by analyzing the apparent fractional fetal DNA concentration using multiple SNP loci. The apparent fetal DNA concentration is the measured fetal DNA concentration at a particular region using a fetal-specific genetic marker. The apparent fetal DNA concentration at a particular region may differ from the actual fetal DNA concentration when at least two of the fetuses are dizygotic. For monozygotic twins, the apparent fractional fetal DNA concentrations would be similar at different SNP loci across the whole genome. However, for dizygotic twins, the apparent fractional fetal DNA concentration would show a bimodal or trimodal distribution because of the difference in the genotypes of the two fetuses. In such methods, haplotype information for the father and/or mother is not required though can be used.

Example Using Apparent Fetal DNA Concentration

FIGS. 6 and 7 illustrate using regional genomic variations in fetal DNA fractions in maternal plasma to reveal the zygosity of twin pregnancies according to embodiments of the present invention. FIG. 6 shows an example where twins are monozygotic, and FIG. 7 shows an example where the twins are dizygotic. The genotypes of the father, mother and the pair of twins (monozygotic or dizygotic) at two SNP loci (locus 1 and locus 2) are shown. These two loci are from different chromosomal regions, and thus are part of two different groups, using the terminology above.

For illustration purpose, we assume that each of the two twin fetuses would contribute 10% of the maternal plasma DNA and there are a total of 100 genome-equivalents of DNA in the maternal plasma sample. One genome-equivalent is the amount of DNA that is contained in a euploid human cell. In other scenarios, the two fetuses each contribute different amounts of DNA to the biological sample (e.g. maternal plasma).

For monozygotic twins (as shown in FIG. 6), their genetic compositions are identical. Thus, both twins are heterozygous at both locus 1 and locus 2, and any other loci suitable for determining the apparent fractional fetal DNA concentration by quantifying both the shared and the fetal specific alleles in the maternal plasma sample. For locus 1, 180 molecules carrying the A allele and 20 molecules carrying the T allele are present in the maternal plasma, hence, giving rise to an apparent fractional fetal DNA concentration of 20% [20×2/(180+20)]. For locus 2, an apparent fractional fetal DNA concentration of 20% is also detected by quantifying the G and C alleles. As the genetic makeup of the two twin fetuses are identical, when twin 1 is heterozygous at a particular SNP locus, twin 2 would also be heterozygous at the same SNP locus. Therefore, the apparent fractional fetal DNA concentration measured at any SNP locus across the whole genome would be similar.

For dizygotic twins, the genotypes for at least part of the genome would be different. As illustrated in FIG. 7, both twin 1 and twin 2 are heterozygous at locus 1, hence, giving an apparent fractional fetal DNA concentration of 20%. On the other hand, twin 1 is homozygous for the G allele at locus 2 while twin 2 is heterozygous. As a result, the apparent fractional fetal DNA concentration at locus 2 is 10% [10×2/(10+190)] based on the quantities of the G and C alleles. In other words, when both fetuses are heterozygous at a locus, the apparent fractional fetal DNA concentration would be 20%. However, when only one fetus is heterozygous at a locus, the apparent fractional fetal DNA concentration would be reduced (e.g. 10% if the amount of fetal DNA released by each member of the twins is equal). Therefore, when the apparent fractional fetal DNA concentrations are measured at multiple SNP loci, there would be a bimodal distribution when both fetuses contribute equal amounts of fetal DNA. It is possible that each member of the twins would release different amounts of DNA into the maternal plasma. In this scenario, a trimodal distribution of fractional fetal DNA concentrations would be seen when the maternal plasma DNA is analyzed, which is discussed below.

D. Other Techniques for Measuring Expected Value

As mentioned above, the expected value (e.g. the actual fractional fetal DNA concentration) can be determined from genetic measurements at other chromosomal regions. Another approach for measuring this variation is to compare the fractional concentration of fetal DNA (or some other parameter) determined using genetic markers to one that is measured using another approach, such as one that is based on markers which are not genetic in nature. Thus, the expected value (e.g. the total fractional fetal DNA concentration from all fetuses) could also be determined by other measurements. One embodiment involves the measurement of the amount of a placenta-specific epigenetic marker, e.g. DNA methylation, in the biological samples.

In one embodiment, the fractional concentration of fetal DNA can be measured using an epigenetic marker. In one implementation, the epigenetic marker can be a DNA methylation marker. One example of a fetal DNA methylation marker is one that exhibits differential DNA methylation patterns between the fetal-derived and maternal-derived DNA in plasma (U.S. Pat. No. 6,927,028). One example of such a marker is the SERPINB5 gene, coding for maspin, which is hypomethylated in fetal DNA present in maternal plasma, but hypermethylated for the maternal DNA in maternal plasma (U.S. Pat. No. 8,026,067). Another example is the RASSF1A gene which is hypermethylated in fetal DNA present in maternal plasma, but hypomethylated for the maternal DNA in maternal plasma (U.S. Pat. No. 7,754,428). Other DNA methylation markers are described elsewhere (Papageorgiou E A et al. *Am J Pathol* 2009; 174: 1609-1618).

Such DNA methylation markers can be detected in maternal plasma using a number of techniques well known to those skilled in the art, including methylation-specific PCR (Herman J G, et al. *Proc Natl Acad Sci USA* 1996; 93: 9821-9826), real-time methylation-specific PCR (Lo Y M D et al. *Cancer Res* 1999; 59: 3899-3903) or MethyLight (Eads C et al. *Nucleic Acids Res* 2000; 28: E32), bisulfite sequencing (Frommer M. *Proc Natl Acad Sci USA* 1992; 89: 1827-1831), methylation-sensitive restriction enzyme digestion (Chan K C A et al. *Clin Chem* 2006; 52: 2211-2218), methyl-BEAMing (Li M et al. *Nat Biotechnol* 2009; 27: 858-863), and massively parallel sequencing (Komori H K et al. *Genome Res* 2011; 21: 1738-1745).

As an example, using RASSF1A as a molecular marker, one can calculate the fractional fetal DNA concentration in maternal plasma by measuring the proportion of hypermethylated RASSF1A sequences over the total (i.e. hypermethylated plus hypomethylated) RASSF1A sequences in maternal plasma. For monozygotic twin pregnancies, the fractional fetal DNA concentration in maternal plasma measured using one or a series of fetal genetic markers across different parts of the genome should have a close correlation with that measured using the RASSF1A DNA methylation marker system as described in the first sentence of this paragraph. However, for dizygotic twin pregnancies, the correlation between the fractional fetal DNA concentrations measured using the fetal genetic markers should exhibit a weaker correlation with the RASSF1A DNA methylation marker system. In one embodiment, one could analyze the correlation between the genetic and DNA methylation marker system using a series of each of these types of markers. For example, the correlation can be examined using Pearson correlation or linear regression. Other types of epigenetic markers include those based on histone modifications, such as methylation and acetylation.

Another embodiment is to measure the amount of a genetic sequence that is present in the fetal genome but absent in the maternal genome. Examples of such genetic sequences include the RHD gene for pregnancies where the mother is RhD-negative and the father is homozygously positive for RHD. Thus, if all fetuses are RhD-positive and the mother is RhD-negative, the RHD gene can be used to determine the actual fetal DNA concentration. Another example is the measurement of the amount of chromosome Y sequences in multi-fetus pregnancies involving only male fetuses. For instance, if all of the fetuses are male, then the actual fetal DNA concentration can be measured using a locus on the Y chromosome.

Thus, one embodiment can calculate the expected value (e.g. a fetal DNA concentration) using genetic markers by measuring a third amount of DNA fragments having a fetal-specific sequence selected from one or more fetal-specific sequences. Since the calculation is of an expected value (e.g. a fetal DNA concentration) if the fetuses are genetically identical, all of the fetuses have the fetal-specific sequence (e.g. one of the examples above). A normalized value for the third amount is obtained, e.g., via ways described herein to determine a normalized parameter. The normalized value can then be used as the expected value (e.g. the fetal DNA concentration). One implementation identifies one or more second loci at which the fetuses have a respective first allele and the mother does not have the respective first allele. The fetal-specific sequences are then the respective first alleles. The normalized value for the third amount can be obtained by measuring a total amount of alleles at the one or more second loci, and calculating the fetal DNA concentration from a ratio of the third amount and the total amount.

E. Non-Polymorphic Fetal-Specific Sequences

In another embodiment, non-polymorphic fetal-specific sequences could be used to measure the apparent fractional fetal DNA concentration. For example, the amount of chromosome Y sequences in a maternal plasma sample could be measured with reference to a non-fetal specific sequence, for example the LEP gene coding for leptin. The chromosome Y to LEP DNA ratio could be compared to an expected value, for example a total fractional fetal DNA concentration as measured with the use of a placenta-specific DNA methylation marker. If the fractional chromosome Y concentration differs from the expected value, it implies that the pregnancy involves at least one set of dizygotic fetuses and at least one fetus is a male, as well as at least one fetus is a female. Besides fractional chromosome Y amount, absolute values of the amount of chromosome Y sequences in a maternal plasma sample could also be used as the measurement to determine zygosity as described later below.

Accordingly, a first amount of one or more fetal-specific sequences (which can include non-polymorphic sequences) can be measured in the biological sample at one or more first loci. A normalized parameter for the first amount can be obtained, and then used as described herein to determine whether at least two of the fetuses are dizygotic.

F. Absolute Fetal DNA Concentration

As an alternative to fractional fetal DNA concentration, one can use the absolute values for the measurement (e.g. counts) of the secondary alleles for a chromosomal region, as long as some calibration (an implicit normalization) is performed. Such a use is termed "absolute" in a sense that an explicit fraction is not calculated. For example, if the measuring step can be calibrated such that a certain amount of DNA fragments from a region can be controlled or correlated from one experiment to another, the amount of the primary alleles may implicitly be determined as the total minus the second amount for the secondary alleles. Besides knowing an absolute value for the amount (e.g. number) of DNA fragments for a region (i.e. for specific loci of the region), a fixed ratio of DNA fragments from one region to another can provide the calibration. For example, a protocol can call for preparing a sample in a specified manner, such that the total number of DNA fragments from a first region is 1.4 times the number of total number of DNA fragments for a second region. This scaling factor can then be used as part of the comparison. In one embodiment, a known amount of a DNA or other types of calibrator can be added to the biological sample.

In this manner, the amount of the secondary alleles (or other fetal-specific genetic markers) from different chromosomal regions can be directly compared to each other. In such a situation, the parameter is still effectively calculated using the first amount of the primary alleles, but such a value disappears due to the calibration (i.e. the first amount, or the first amount plus the second amount are the same, and thus they cancel out of the equation). For example, apart from counting digital PCR results or analyzing sequencing data, the markers can also be measured by an appropriately constructed calibration curve such that the markers would be calibrated to give the same quantitative readout if the target concentrations are the same. In a similar manner, the first amount of the primary alleles from different chromosomal regions can be compared to each other, and such changes can provide the same results described herein for the amounts of the secondary allele, since the first amount will vary inversely with the variance in the second amounts (e.g. two peaks in the first amount would be seen for dizygotic fetuses, compare to FIG. 8).

Accordingly, for a given set of such fetal-specific genetic markers, their correlation in monozygotic and dizygotic twin pregnancies would be different. In one embodiment, the markers are quantified using digital PCR, in which case they would all give the same or similar measured amounts in monozygotic twin pregnancies. Conversely, in dizygotic twin pregnancies, a proportion of such markers would give more divergent results. For the sake of illustration, assume both fetuses in a dizygotic pregnancy release the same concentration of fetal DNA into maternal plasma (although that is not necessarily the case). Then for a first marker in which both fetuses have inherited the same paternally-inherited allele that is absent in the mother's genome, the measured amount of the first marker (e.g. a secondary allele when the mother is homozygous) should be twice of the amount measured by a second marker in which only one of the fetuses has inherited a paternally-inherited allele that is absent in the mother's genome. For dizygotic twins each releasing a different amount of fetal DNA, the measured amount of the first marker would be more than that of the second marker but the two values would not differ by 2-fold.

As an example of a calibration procedure, with the use of digital PCR analysis, quantification for a fetal-specific allele at locus 1 and the quantification for another fetal-specific allele at locus 2 could be performed using the same maternal plasma DNA sample and at the same average template molecule concentration per digital PCR reaction. In such a scenario, the background amount of non-fetal DNA is the same for locus 1 and locus 2. Hence, one could simply count the number of digital PCR wells positive for the fetal-specific allele at locus 1 to determine the apparent absolute amount of fetal DNA at locus 1. The same process could be performed at locus 2 to determine the apparent absolute amount of fetal DNA. The two absolute values could then be compared with each other (e.g. where one is used as an expected value) or to an expected value determined in another way (e.g. as described above) to determine if a statistically significant difference is present.

G. Detecting Difference in Fetal DNA Concentrations

Figure 8:
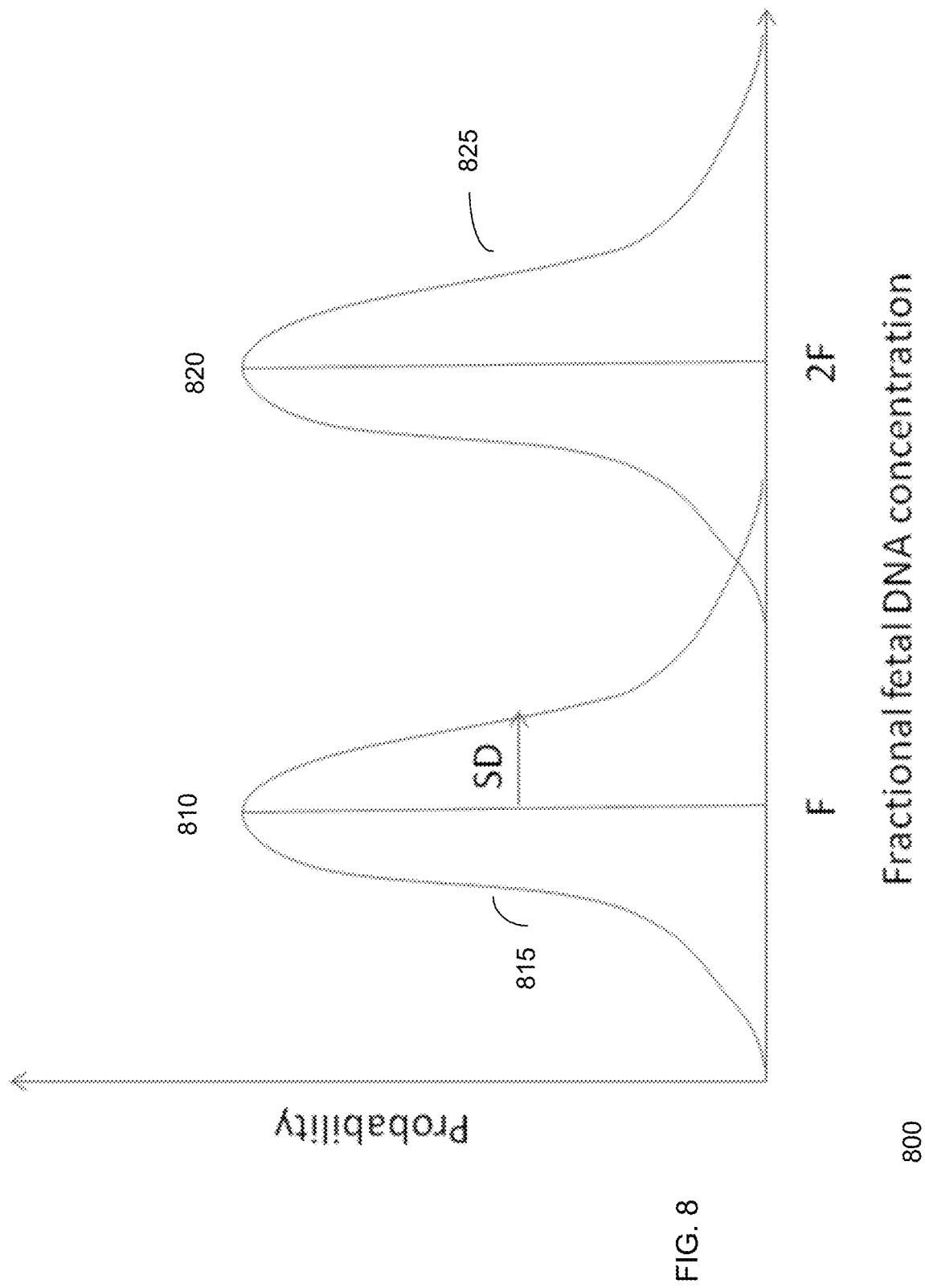
FIG. 8 shows an example histogram of fetal DNA concentration for dizygotic twins contributing equal amounts of fetal DNA according to embodiments of the present invention.

FIG. 8 shows an example histogram 800 of fetal DNA concentration for dizygotic twins contributing equal amounts of fetal DNA according to embodiments of the present invention. In the histogram, the horizontal (X) axis is the fetal DNA concentration. The measured fetal DNA concentration (absolute or fractional) for a chromosomal region can be used to increment a counter for a range that includes the measured value. As one can see a first peak 810 corresponds to the measured fetal DNA concentration for loci when only one of the fetuses has the fetal-specific allele, while a second peak 820 corresponds to the measured fetal DNA concentration for loci when both of the fetuses has the fetal-specific allele. The peak 820 would correspond to the actual fetal DNA concentration, whereas peak 810 would correspond to an apparent fetal DNA concentration. Since two peaks are seen, one can surmise that fetuses are dizygotic. In one aspect, the relative heights of the peaks can be used to determine zygosity, e.g., as part of step 150.

Histogram 800 can also help to illustrate methods where the actual fetal DNA concentration is measured using techniques other than creating a histogram from parameter values at various chromosomal regions. For instance, the actual fetal DNA concentration can be measured to be 2F % (e.g. using epigenetic means). Then, if a region belonging to peak 810 is analyzed, the measure parameter for the apparent DNA concentration should appear near peak 810, which would be a statistically significant distance away from the value of 2F %.

The locations of the peaks are one example of a statistical value of a group of normalized parameters (fetal DNA concentration in this example), where the group are the data points (i.e. the counts of the normalized parameters) for one of the curves 815 and 820. For example, peak 820 is a statistical value for the group of normalized parameters represented by curve 825, and peak 820 may be used as the expected value. Note that curves 815 and 825 (when fit to underlying data) are examples of probability distributions and components of a mixture model, as will be discussed later.

Determining how many read counts are required for the differentiation of one from two different fractional fetal DNA concentrations can proceed as follows. Assume that each of the two dizygotic twins would contribute F % of maternal DNA. There would be two populations (clusters) of SNP loci showing two different fractional fetal DNA concentrations in the maternal plasma. In one population of SNPs, the apparent fractional concentration is F % while in the other population of SNPs, the apparent fractional concentration is 2F %. The standard deviation (SD) of the distribution of the prior set of SNP loci would be $$\sqrt{\frac{F\%(1-F\%)}{N}},$$

where N is the total number of reads aligning to this set of SNP loci. The SD of the latter group of SNP loci would also be approximately equal to $$\sqrt{\frac{F\%(1-F\%)}{N}}.$$

The two populations of SNP loci can be differentiated with less than 5% overlapping if $$2F\% - F\% > 4x\sqrt{\frac{F\%(1-F\%)}{N}}.$$

Therefore, $N > 16(1-F\%)/F\%$.

Table 2 shows the required number of sequence reads to discriminate the two apparent fractional fetal DNA concentrations (F % vs 2F %) resulting from two populations of SNP loci for various values of F %.

TABLE 2

| Fractional fetal DNA concentration (F) (%) | No of sequence reads required |
|---|---|
| 1 | 1584 |
| 2 | 784 |
| 3 | 517 |
| 4 | 384 |
| 5 | 304 |
| 6 | 251 |
| 7 | 213 |
| 8 | 184 |
| 9 | 162 |
| 10 | 144 |
| 15 | 91 |
| 20 | 64 |
| 25 | 48 |
| 30 | 37 |

H. Different Peaks for Each Fetus

It is possible that each member of the twins would release different amounts of DNA into the maternal plasma. In this scenario, a trimodal distribution of fractional fetal DNA concentration would be seen when the maternal plasma DNA is analyzed. Two of the three peaks would represent the fractional fetal DNA concentration contributed by each of the two individual twin fetuses whereas the third peak would represent the total sum of the fractional fetal DNA of the two fetuses in total. Thus, embodiments can also provide a method whereby the relative amounts of DNA released by each member of the twins can be deduced.

It is likely that a large discrepancy in the amounts of DNA released by each twin might be associated with an adverse outcome, e.g., the imminent demise of one of the twins. The different contributions of fetal DNA of each fetus can be tracked over time to monitor the health of the fetuses. Another utility of the relative amounts of DNA released by each twin would be if one is using massively parallel sequencing of maternal plasma DNA for the detection of fetal chromosomal aneuploidy, e.g. trisomy 21 (Chiu R W K et al. *Proc Natl Acad Sci USA* 2008; 105: 20458-20463; Fan H C et al. *Proc Natl Acad Sci USA* 2008; 105: 16266-16271; Sehnert A J et al. *Clin Chem* 2011; 57: 1042-1049; Sparks A B et al. *Am J Obstet Gynecol* 2012; doi: 10.1016/j.a-jog.2012.01.030). The fractional fetal DNA concentration is an important parameter in the diagnostic sensitivity of such approaches.

Hence, if the twins can be shown to be monozygotic, then one can essentially just use the same algorithm for handling the massively parallel sequencing data for the noninvasive detection of fetal trisomy 21. On the other hand, if the case involves dizygotic twins, then one can first measure the relative proportion of fetal DNA contributed by each twin; and then see if the fractional fetal DNA concentration of the twin that has released the lesser amount of DNA into maternal plasma might be detectable at the depth of sequencing that is used. One can increase the depth of sequencing if necessary. In other words, embodiments allow fetal chromosomal aneuploidy screening to be carried out even for twin pregnancies.

As an illustration, assuming that in a particular dizygotic twin pregnancy, fetus 1 and fetus 2 contribute 3% and 2%, respectively, of the DNA in the pregnant mother's plasma. Assuming that one wishes to carry out trisomy 21 detection using massively parallel sequencing of the mother's plasma (Chiu R W K et al. *Proc Natl Acad Sci USA* 2008; 105: 20458-20463). Using an embodiment would allow us to determine the fractional fetal DNA concentrations of 3% and 2%, as well as the fractional fetal DNA concentration contributed by both fetuses together, i.e., 5%. The depth of sequencing that one would need to do to allow robust trisomy 21 detection would be one that is sufficient to detect a trisomy 21 fetus if the fractional fetal DNA concentration is 2%. A relationship between the depth of sequencing needed and the fractional concentration of fetal DNA has previously been reported (Fan H C et al. *PLoS ONE* 2010; 5: e10439; Chiu R W K et al. *BMJ* 2011; 342: c7401). A similar consideration can also be applied for the prenatal detection of trisomy 13, trisomy 18 (Chen E Z et al. *PLoS ONE* 2011; 6: e21791; Palomaki G E et al. *Genet Med* 2012; doi: 10.1038/gim.2011.73), sex chromosome aneuploidies (Lau T K et al. *J Matern Fetal Neonatal Med* 2011; doi: 10.3109/14767058.2011.635730, chromosomal translocations (Lun F M et al. *Clin Chem* 2011; 57: 917-919) and chromosomal microdeletions (Peters D et al. *N Engl J Med* 2011; 365: 1847-1848).

Accordingly, the calculation of fractional fetal DNA concentration can be essential for other applications of prenatal diagnosis. For example, the accuracy of noninvasive prenatal diagnosis by maternal plasma analysis can be dependent on the fractional concentration of the DNA contributed by the fetus intended to be assessed in the maternal plasma sample. For the prenatal detection of chromosomal aneuploidy, the additional chromosome dosage of the affected chromosome in maternal plasma is proportional to the fractional fetal DNA concentration. The fractional fetal DNA concentration contributed by each of the two fetuses can be determined as follows using techniques described above.

Figure 9:
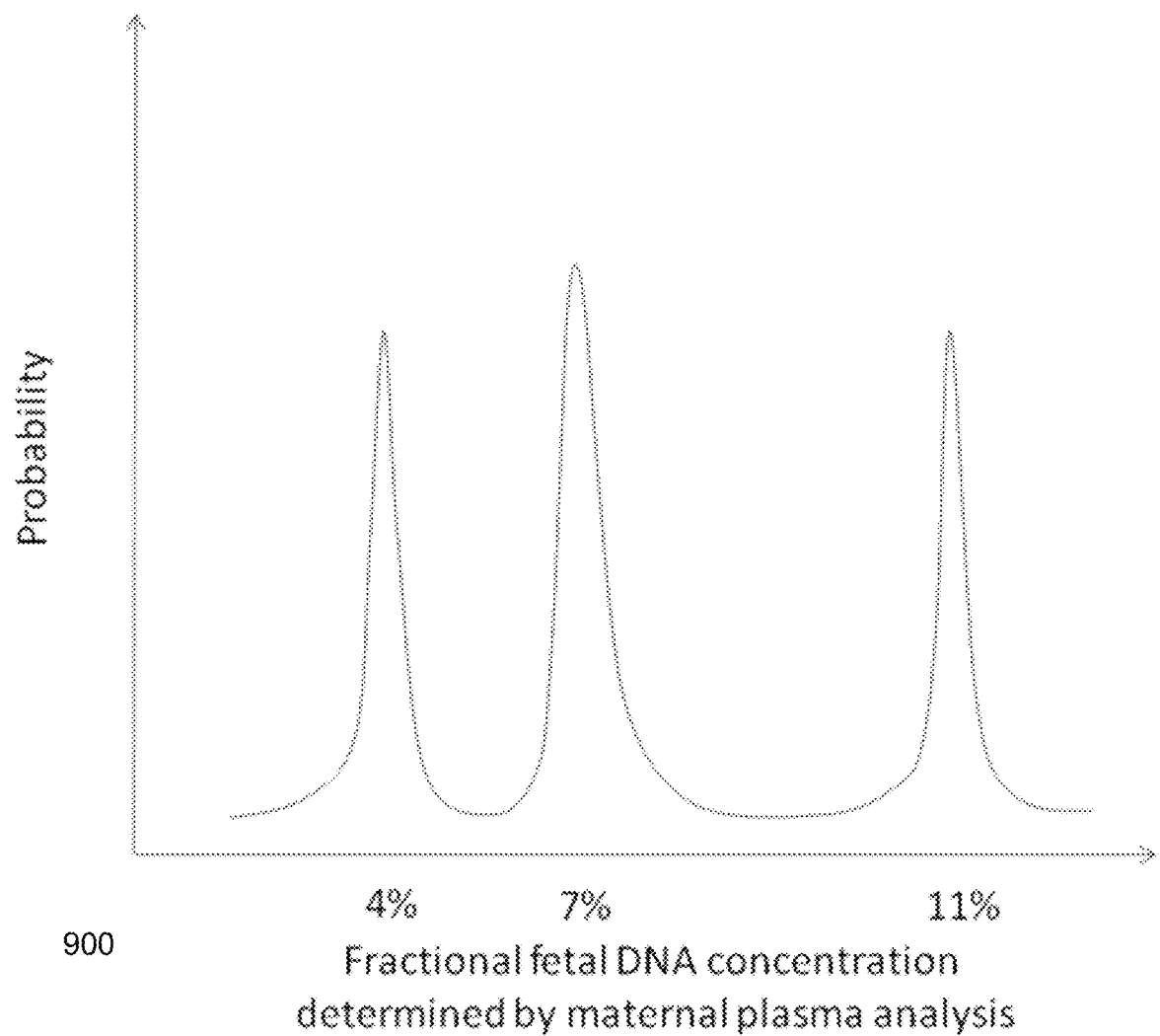
FIG. 9 shows a histogram for a fractional fetal DNA distribution based on SNP analysis when the two fetuses contribute different amounts of DNA to the maternal plasma sample according to embodiments of the present invention.

FIG. 9 shows a histogram 900 for fractional fetal DNA distribution based on SNP analysis when the two fetuses contribute different amounts of DNA to the maternal plasma sample according to embodiments of the present invention. Three peaks of fractional fetal DNA concentrations are observed and correspond to fractional concentrations of 4%, 7% and 11%. The first two peaks would correspond to the fractional concentration contributed by each of the two fetuses because when only one of the fetuses is heterozygous at a SNP locus for which the mother is homozygous, the fraction contributed by the fetal-specific allele would be useful for reflecting the fractional fetal DNA concentration of that particular twin fetus. The last peak corresponds to the SNP loci which both fetuses are heterozygous but the mother is homozygous. The fractional fetal DNA concentration calculated using these SNP loci would be the total fractional fetal DNA concentration contributed by both fetuses. For any application which requires a minimal fractional fetal DNA concentration so as to make an accurate diagnosis, the lowest of the three figures would be relevant as this would reflect the fractional concentration of fetal DNA from the fetus with the least contribution of DNA to the maternal plasma sample. The depth of sequencing could then be adjusted to provide a statistically robust diagnostic result given the fractional fetal DNA concentration of the latter fetus.

I. Using Statistical Variation for Entire Population

In one embodiment, the value of SD for the combined population of the two or more peaks can be used to determine zygosity. For monozygotic fetuses, the SD (an example of a measure in the spread of parameter values) would be smaller than the SD for dizygotic twins. This is because the underlying data is really from two peaks, and thus the parameter values would be more diverse than if there was one peak and the spread in measured parameter values was simply due to statistical variation. Such a technique would not require the identification of the separate populations of loci within a particular maternal genotype. For example, one may still need to distinguish regions where the mother is heterozygous from regions where the mother is homozygous, for loci where two alleles are detected.

Thus, in dizygotic twin pregnancies, the fractional concentrations of fetal DNA in maternal plasma or serum, as measured by each or a selected combinations of a fractional concentration of a series of fetal-specific genetic markers in comparison to the total DNA in maternal plasma, would exhibit a larger variation than the fractional concentration in monozygotic twin pregnancies. The variation can be measured by statistical methods well-known to those skilled in the art, such as the SD, the range, the inter-quartile range, etc.

Accordingly, the standard deviation or other variance in the normalized parameters (e.g., as calculated in step 440) can be used to determine zygosity. The variance can be compared to a threshold value, and if the variance exceeds the threshold, then it can be determined that at least two of the fetuses are dizygotic. The act of comparing a normalized parameter to a cutoff value to determine if the normalized parameter is statistically different from an expected value is effectively accomplished by the computation of the variance and the comparison to the threshold.

J. Considerations for Meiotic Recombination

As mentioned above, the loci within the chromosomal region can be chosen such that the chance of recombination between the loci is low, e.g., less than 1%. The example below addresses issues that arise when recombination occurs between the loci of a chromosomal region.

As described above, for any chromosomal region, when the two fetuses inherit the same paternal haplotype, the apparent fractional fetal DNA concentration calculated based on the fetal-specific alleles would represent the total DNA contributed by the two fetuses. On the other hand, when the two fetuses inherit different paternal haplotypes from the father, at any SNP locus that the father is heterozygous (AB) and the mother is homozygous (AA), only one of the fetuses would contribute the fetal-specific allele to the maternal plasma. As a result, the apparent fractional fetal DNA concentration measured at these loci would be lower than the value measured at loci where both fetuses inherit the same paternal haplotype.

Figure 10:
FIG. 10 shows an example of the effect of recombination on the apparent fractional fetal DNA concentration in a pregnant woman carrying a pair of dizygotic twins.

FIG. 10 shows an example of the effect of recombination on the apparent fractional fetal DNA concentration in a pregnant woman carrying a pair of dizygotic twins. In this example, there is a recombination between paternal Hap III and Hap IV when the paternal haplotype is passed on to Twin 1. The recombination occurs between SNP loci 3 and 4. Effectively, Twin 1 inherits the Hap III for loci 1 to 3 and the Hap IV for loci 4 to 6. Twin 2 inherits Hap IV from the father without any recombination.

During the analysis of fractional fetal DNA concentration for this pregnant woman, only 1, 2, 3 and 5 are informative because the fetal-specific allele (B allele) would be present in the maternal plasma. Loci 4 and 6 would become noninformative because both fetuses inherit the A allele from the father which is identical to the maternal allele. On the other hand, at locus 5, both fetuses inherited the B allele from the father, leading to a higher apparent fetal DNA compared with the values determined for loci 1 to 3. If the whole region (involving loci 1 to 6) is used for the analysis of apparent fetal DNA concentration, the estimated concentration would be between the apparent fractional fetal DNA concentrations for regions that both fetuses inherit the same paternal haplotype and regions that the two fetuses inherit different paternal haplotypes.

IV. Deductive SNP Calling

The sections above described examples for identifying zygosity when genotype information for both parents were known, and when just the genotype of the mother was known. However, embodiments (e.g. methods 100 and 400) can be applied when no genotype information is known about the parents. In such a situation, the measured parameter values can be grouped so as to identify the maternal genotype, or at least the most likely maternal genotype. In this manner, no a priori knowledge needs to be known before the analysis of the biological sample taken from the mother. Therefore, embodiments can deduce the maternal genotype, and the fetal genotypes. Note that some of the regions can remain unclassified.

Once at least some of chromosomal regions are classified (e.g., into a group where the mother is homozygous and at least one of the fetuses is heterozygous), methods described herein can be used for determining the zygosity of the fetuses. For example, the determination of whether a pair of twins are monozygotic or dizygotic can be achieved by analyzing the apparent fractional fetal DNA concentration (or other parameter) using multiple SNP loci. For monozygotic twins, the apparent fractional fetal DNA concentrations would be similar at different SNP loci across the whole genome. However, for dizygotic twins, the apparent fractional fetal DNA concentration would show a bimodal distribution because of the difference in the genotypes of the two fetuses.

Besides determining the zygosity, the fetal DNA concentration can also be determined from the genetic analysis, which as described above is complicated due to the multiple pregnancies. As mentioned above, the fetal DNA concentration is useful for other noninvasive fetal diagnostic techniques besides determining zygosity.

A. Method

In order to determine the fractional fetal DNA concentration directly from sequencing data (e.g. with high fold coverage) or PCR data, we define the variable ratio $\hat{\mu}_i$ at SNP site i:

$$\hat{\mu}_i = \frac{b_i}{a_i + b_i}$$

wnere $a_i$ is me maximal counts of a specific allele (i.e. primary allele) at SNP locus (site) i, and $b_i$ is the secondary maximal counts of another allele (i.e. secondary allele) over SNP locus i. This value is half of the apparent fetal DNA concentration using the formula above for loci where the mother is homozygous. This technique is also usable with other normalized parameters, including the absolute fetal DNA concentration, as described above.

Considering SNP sites (or other polymorphic sites) in maternal plasma of a singleton pregnancy, these SNP sites can be classified into four categories based on maternal genotype and fetal genotype combinations, so-called maternal-fetal mixed genotypes, implicitly in form of $AA_{AA}$, $AA_{AB}$, $AB_{AA}$ and $AB_{AB}$ where the superscript represents the maternal genotype, and the subscript represents fetal genotype. AA indicates homozygosity and AB indicates heterozygosity. Thus, the measurement at each SNP locus i is composed of the number of allele A occurrences ($a_i$) which corresponds to the maximal counts and the number of allele B occurrences ($b_i$)) corresponds to secondary maximal counts from the sequencing data. The fractional fetal DNA concentration will influence the $\hat{\mu}_i$ at each of the SNP sites for the categories $AA_{AB}$ and $AB_{AA}$. In theory, $\hat{\mu}_i$ for category $AA_{AA}$ is 0 and $\hat{\mu}_i$ for category $AB_{AB}$ is 0.5. Thus, the fractional fetal DNA concentration can determine the distribution of maternal-fetal mixed genotypes in maternal plasma. In principle, the optimal estimation of the fractional fetal DNA concentration will produce a distribution which generates the observed profile of $\hat{\mu}_i$ with the highest probability.

Embodiments can distinguish between the four categories and perform a further analysis of categories $AA_{AB}$ and $AB_{AA}$, as described above, e.g., in method 400. As part of distinguishing between the different categories (i.e. which chromosomal region belongs to which category), embodiments can determine a fetal DNA concentration by finding an optimal concentration that best fits the data to a linear combination of probability distributions.

Figure 11:
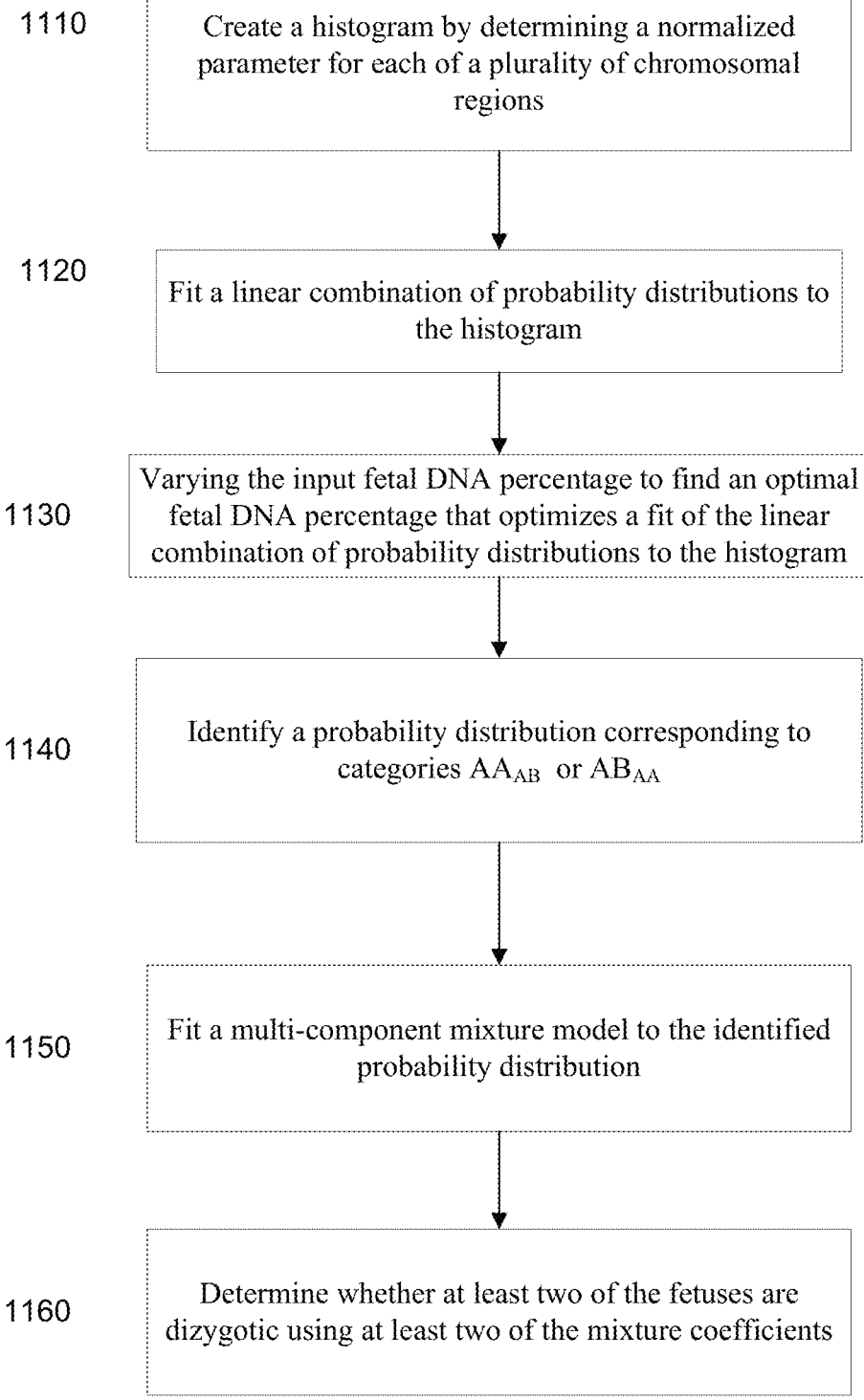
FIG. 11 is a flowchart illustrating a method 1100 of determining a fetal DNA percentage in a biological sample from a pregnant female with at least two fetuses and determining whether at least two of the fetuses are dizygotic according to embodiments of the present invention.

FIG. 11 is a flowchart illustrating a method 1100 of determining a fetal DNA percentage in a biological sample from a pregnant female with at least two fetuses and determining whether at least two of the fetuses are dizygotic according to embodiments of the present invention. The biological sample comprises fetal and maternal DNA.

In step 1110, a histogram is created by determining a normalized parameter for each of a plurality of chromosomal regions (e.g., as described above for method 400). For each of a plurality of chromosomal regions, one or more loci in the respective chromosomal region are identified at which a respective first allele and a respective second allele are detected in the biological sample. Such regions correspond to the four different categories described above.

The alleles may be detected in any suitable manner, and a statistically significant amount of each allele can be ensured. A first amount of the one or more first alleles and/or a second amount of the one or more second alleles are measured in the biological sample at the one or more loci. The first allele among the loci can be a different allele, as can be the second allele. In one implementation, if the first allele is more abundant than the second allele at a particular locus in a chromosomal region, then all of the first alleles are more abundant than the second allele at the respective locus. In such a manner, the counts of alleles from multiple loci can be combined.

A normalized parameter for the first amount or the second amount is obtained. The normalized parameter can be of any type as described herein. For example, the normalized parameter can be determined from the first amount and the second amount, and provided a relative measure between the first amount and the second amount. An example includes the fractional fetal DNA concentration. The normalized parameter can also be the absolute fetal DNA concentration, as can be determined with the proper calibration. In one embodiment, $\hat{\mu}_i$ as defined above is used.

Once the normalized parameters are determined for each of the chromosomal regions, these data points can be used to create the histogram. The data structure of the histogram can be created by separating the possible values of the normalized parameter into a number of sub-ranges. For example, if the range is between 0 and 0.5, the sub-ranges can be of size 0.01 each. A counter can be associated with each sub-range. The counters can then be incremented based on a number of chromosomal regions with specified values (i.e. for values within the corresponding sub-range) for the normalized parameter.

In step 1120, a linear combination of probability distributions is fit to the histogram. For example, two probability distributions can be used to fit the data for categories $AA_{AB}$ and $AB_{AA}$. As described below, the location of the data points for each of these categories is dependent on the fetal DNA percentage. Thus, the fetal DNA percentage is an input to the linear combination of probability distributions. Distributions for the other categories may also be used, e.g., as described below.

In another embodiment, the data points can already be limited to a particular category $AA_{AB}$ and $AB_{AA}$. For twin pregnancy, the number of distributions would be two if both fetuses contribute equal amounts of DNA to the biological plasma or three if the two fetuses contribute different amounts of DNA to the maternal plasma. For pregnancies involving 3 or more fetuses, the number of distributions would be equal to the number of fetuses if each fetus contributes an equal amount of DNA to the maternal plasma. In such an embodiment, step 1150 can be skipped as redundant, and step 1160 would use the coefficients of the probability distributions.

In step 1130, the input fetal DNA percentage ø is varied to find an optimal fetal DNA percentage that optimizes a fit of the linear combination of probability distributions to the histogram. The term "optimal" is defined above. As part of the optimization process, an error can be determined between the data and the linear combination of probability distributions. This error term can be used to determine when the value of ø provides a sufficient fit to the data (i.e. the error is small enough that the value of ø called optimal).

In step 1140, once the fetal DNA percentage ø is known, a probability distribution corresponding to loci at which the mother is homozygous and at least one of the fetuses is heterozygous or corresponding to loci at which the mother is heterozygous and at least one of the fetuses is homozygous is identified. For example, if two linear combinations are used, the fetal DNA percentage ø can provide an approximate location for the peak of the distribution. As the fetuses may be dizygotic (or at least two of them), the peak would not be at the exact location predicted by ø but the two distributions can be differentiated. For example, the distribution with the peak closest to the value of ø/2 would be for category $AA_{AB}$, and the distribution with the peak closest to 0.5-ø/2 would be for $AB_{AA}$.

In step 1150, a multi-component mixture model is fit to the identified probability distribution. The multi-component mixture model includes a mixture coefficient for each of a plurality of components. In one aspect, the components correspond to the peaks in FIG. 8 or 9. A component can be defined using any suitable functional form, such as Gaussian, where each component would correspond to a different Gaussian function.

As is mentioned below, an additional peak would result with triplets. One way to determine the number of components in the mixture model is letting the number of components equal the number of fetuses if the fetuses contribute equal amounts of DNA to the maternal plasma (e.g., to account for the regions showing the actual fetal DNA concentration). Alternatively, Bayesian information criterion (BIC) or Akaike information criterion (AIC) may be used to determine the number of components to the mixture model. Thus, the mixture model can have two components for twins that contribute the same amount of fetal DNA or a higher number of components when each of the twins contribute differing amounts of DNA, or for pregnancies involving more than two fetuses.

In one embodiment, the identified distribution can be found by genotyping the mother so as to determine the category $AA_{AB}$ or $AB_{AA}$ in that manner. In such an embodiment, steps 1130 and 1140 would not be done. Also, the value of 0 could be determined by other ways, e.g., using epigenetic markers. Conversely, the genotype of the mother at a particular chromosomal region can be identified by determining the probability distribution that corresponds to the particular chromosomal region. For example, one can determine the probability distribution that has the highest value for the normalized parameter of the particular chromosomal region, and use that probability distribution to determine the maternal genotype. As the probability distributions depend differently based on the fetal DNA percentage, the corresponding maternal genotype is straightforward to determine.

Similarly, the genotype of the fetuses at a particular chromosomal region can be identified by determining the probability distribution (which may be a component of the mixture model) that corresponds to the particular chromosomal region. For example, one can determine the probability distribution that has the highest value for the normalized parameter of the particular chromosomal region, and use that probability distribution to determine the number of fetuses being heterozygous at the respective SNP loci. As the probability distributions depend on the number of fetuses being heterozygous at the respective SNP loci and also the fetal DNA percentage, the genotype information of the fetuses can be deduced.

In step 1160, it is determined whether at least two of the fetuses are dizygotic using at least two of the mixture coefficients. For example, at least two of the mixture coefficients can be compared to a threshold. The value of the coefficients can be used to determine whether a peak actually exists. If a peak is small, then the mixture coefficient will be small, and one can assume that an additional peak does not actually exist (e.g. the peak that would occur at F % if 2F % is the actual fetal DNA percentage). In that case, the mixture model would convey that only one peak actually exists, and the fetuses are monozygotic. If two of the mixture coefficients are above the threshold, then at least two peaks actually exist, and at least two of the fetuses are dizygotic. The threshold can be an absolute value or a relative value compared to the coefficients of the other components (e.g. the threshold can depend on the value of one or more of the coefficients, e.g., a percentage of the maximum value or overage of the coefficients). Note that the term "coefficient" encompasses any scaling factor that multiplies a coefficient or is implicit in the component. If three components are used (e.g. because the individual contributions of each fetus to the total fetal DNA percentage is desired or because triplets are being tested), the determination of dizygosity can be stopped after only two coefficients are tested, since then dizygosity will already have been identified.

In one embodiment, the locations of the peaks of the components of the mixture model are constrained to have a separation gap that exceeds a predetermined value. The separation gap is the distance (as measured in units of the parameter values of the histogram) from one peak to a nearest peak. The predetermined value can depend on a desired accuracy and the outcome one desires. For example, if one wants to simply identify zygosity, then two components for the model may be used (e.g., as a distinction between peaks of the contribution from each individual fetus is not desired), and the predetermined value can be dependent on the determined fetal DNA concentration (e.g., a larger fetal DNA concentration could lead to a larger separation distance). The predetermined value can also be dependent on the number of fetuses, e.g., for triplets the separation of different peaks may be less on a relative basis, since the peaks may roughly correspond to one-third and not one-half of the actual fetal DNA concentration.

The relative size of the peaks can be used. For example, the relative size can indicate whether there are more regions where the fetuses are genetically the same or the fetuses are genetically different. This would be dependent on the selection of the chromosomal regions. However, in the scenario of the fetuses, the number of regions that two dizygotic twins inherit the same paternal haplotype and different paternal haplotypes should be similar if the selection of chromosomal regions is random. Here, using the relative size of the peaks can make the fitting of the data to different distribution curves more accurate.

B. Fractional Fetal DNA Determination by Deductive SNP Calling Analysis

To illustrate the operation of the above principle, we performed targeted sequencing and applied a binomial mixture model to estimate the fetal DNA concentration. Binomial mixture modeling has been successfully applied to identify the single nucleotide variants in tumor genome (Goya R et al. *Bioinformatics* 2010; 26:730-736; Shah S P et al. Nature 2009; 461:809-813). We adopted the model to estimate the fetal DNA concentration in pregnant maternal plasma. We assume a maternal-fetal mixed genotypes $G_i$=k, k∈{$AA_{AA}$, $AA_{AB}$, $AB_{AA}$, $AB_{AB}$} in plasma at a SNP i to be a multinomial random variable. We let $$X_i = \begin{bmatrix} a_i \\ b_i \end{bmatrix}$$

represent allelic counts of the A allele and B allele at SNP position i, where $N_i$=$a_i$+$b_i$ is the observed read depth. We assume the counts at SNP i are produced from a binomial distribution that is conditioned on $G_i$=k, $X_i$~Binom($b_i$=$\mu_k$, $N_i$) where $\mu_k$∈{$\mu AA_{AA_{AA}}$, $\mu_{AA_{AB}}$, $\mu_{AB_{AA}}$, $\mu_{AB_{AB}}$} is an expected distribution of the B allele frequency ($b_i$) in maternal plasma, which is given by:

$$X_i \sim \binom{N_i}{b_i} \mu_k^{b_i}(1-\mu_k)^{a_i} \quad (1)$$

Theoretically $\mu_{AA_{AA}}$ approximates to constant 0, $\mu_{AA_{AB}}$ to half of fetal DNA concentration $$\frac{\phi}{2}, \mu_{AB_{AA}} \text{ to } 0.5 - \frac{\phi}{2} \text{ and } \mu_{AB_{AB}}$$

is close to constant 0.5. For $\mu_{AA_{AA}}$ and $\mu_{AB}^{AB}$, the deviations from the expected constant values 0 and 0.5, respectively, are mainly affected by the sequencing errors and analytical bias, where as for $\mu_{AA_{AB}}$ and $\mu_{AB_{AA}}$, the perturbation from the 0 and 0.5 are largely determined by the fractional fetal DNA concentration. Examples of analytical bias include the GC bias in massively parallel sequencing (Chen E Z et al. *PLoS One* 2011;6:e21791) and alignment bias (Degner J F et al. *Bioinformatics* 2009. 25:3207-3212).

Subsequently, we applied a binomial mixture model to explain the observed allelic counts. For a given SNP i, the mixture distribution of $X_i$, p($X_i$), is derived from a linear combination of the binomial distribution which is weighted by the multinomial $\pi_k$, $0 \leq \pi_k \leq 1$ and $\Sigma_k \pi_k$=1:

$$p(X_i) = \Sigma_{G_k} \pi_k \text{Binom}(X_i|\mu_k, N_i) \quad (2)$$

where $\pi_k$ is the prior probabilities over the maternal-fetal mixed genotypes. In other words, $\pi_k$ represents the prior belief that a randomly selected position will take on each of the genotypes.

The complete data log-likelihood is given by:

$$\log p(X_{1:T}|\mu,\pi) = \Sigma_{i=1}^T \log \Sigma_{G_k}(\pi_k \text{Binom}(X_i|\mu_k, N_i)) \quad (3)$$

where T is the total number of observed SNP positions in maternal plasma, $\pi_k$∈{$\pi_{AA_{AA}}$, $\pi_{AA_{AB}}$, $\pi_{AA_{AA}}$, $\pi_{AA_{AB}}$}. In addition, the likelihood can be further modeled by the mapping quality and base quality (Goya R et al. *Bioinformatics* 2010; 26:730-736) which can potentially improve the accuracy by:

$$\log p(X_{1:T}|\mu,\pi) \propto \Sigma_{i=1}^T \log \Sigma_{G_k} \pi_k \theta_{j=1}^{N_i}(0.5(1-r_j^i)+r_j^i \\ [(1-q_j^i)(1-\mu_k)+q_j^i \mu_k]) \quad (4)$$

where the $r_j^i$ is the mapping quality and $q_j^i$ is the sequencing quality for the $j^{th}$ aligned base at position i. In our default analyses, we modeled the sequencing quality since most of the current mapping software did not yield the mapping quality.

In general, the $\pi_k$ is specified by 0.7, 0.1, 0.1, and 0.1, respectively, according to the population frequencies of the different maternal-fetal mixed genotypes, and can be estimated, for example, using an Affymetrix Genome-Wide Human SNP Array 6.0. The $\mu_k$ is dependent on fractional fetal DNA concentration ø, $0 \leq ø \leq 1$, for both $AA_{AB}$ and $AB_{AA}$. It is unlikely that ø is greater than 0.4 in pregnant maternal plasma (Chiu R W et al. *BMJ* 2011; 342:c7401). Hence, we compute the fractional fetal DNA concentration ø from 0 to 0.5 iteratively, progressing 0.001 or less increment per iteration until the log-likelihood achieved the maxima. When the ø approaches the actual fractional fetal DNA concentration, the log-likelihood is expected to reach a maxima. In other words, the typical ø that maximizes the log-likelihood can explain the observed allelic counts with the highest probability, otherwise we need to repeatedly update the $\pi_k$ and $\mu_k$ until the log-likelihood has reached its maximum as defined above.

The update rules are defined as the following equations when considering $AA_{AA}$ and $AB_{AB}$:

$$\pi^{new}(k) = \frac{\sum_{i=1}^{T} I(G_i = k) + \delta_k}{\sum_j \sum_{i=1}^{T} I(G_i = j) + \delta_j} \quad (5)$$

where the $I(G_i=k)$ is an indicator function to signify whether maternal-fetal mixed genotype k $G_i$ is assigned to $G_i$ at SNP i according to weighted probabilities of the different maternal-fetal mixed genotypes, and:

$$I = \begin{cases} 1 & G_i = k \\ 0 & G_i \neq k \end{cases} \quad (6)$$

$$\mu^{new}(k) = \frac{\sum_{i=1}^{T} a_i^{I(G_1=k)} + \alpha_k - 1}{\sum_{j \in \{AA_{AA}, AA_{AB}, AB_{AA}, AB_{AB}\}} \sum_{i=1}^{T} N_i^{I(G_i=j)} + \alpha_k + \beta_k - 2} \quad (7)$$

while $AA_{AB}$ and $AB_{AA}$ are under constraint of the fractional fetal DNA concentration in plasma, thus:

$$\mu^{new}(AA_{AB}) = \frac{\phi}{2} \quad (8)$$

$$\mu^{new}(AB_{AA}) = \mu^{new}(AB_{AB}) - \frac{\phi}{2} \quad (9)$$

In addition, for the above formulas (6)~(9), $\mu_k$ is distributed according to a beta distribution $\mu_k \sim \text{beta}(\mu_k|\alpha_k, \beta_k)$. We set $\alpha_k=\{10000, 9500, 5500, 5000\}$ and $\beta_k=\{1, 500, 4500, 5000\}$ corresponding to $G_k \in \{AA_{AA}, AA_{AB}, AB_{AA}, AB_{AB}\}$, respectively, to initialize the $\mu_k$ by $$\frac{\beta_k}{\alpha_k + \beta_k},$$

because we reason that the $\mu_k$ is expected to fluctuate around $\{0, 0.05, 0.45, 0.5\}$ and is adjusted by the real observed distribution of $\hat{\mu}_i \cdot \pi I_k$ is distributed according to a Dirichlet distribution: $\pi_k \sim \text{beta}(\pi_k|\delta_k)$. $\pi_k$ is initialized by $$\frac{\delta_k}{\sum_j \delta_j}$$

where $\delta_k$ is set by a weighting vector $\{7, 1, 1, 1\}$ by default, which represents the proportion of $G_k$ in pregnant maternal plasma and thus indicated the prior belief that a randomly selected position will be assigned to each of the genotypes.

Once the parameters $\pi_k$ and $\pi_k$ are fitted by observed allelic counts, we can apply Bayes' theorem to calculate the posterior probabilities over maternal-fetal mixed genotypes, $\gamma_k = \Pr(G_k|\alpha_i, N_i, \pi_k, \mu_k)$ where:

$$\gamma_k = \frac{\pi_k \text{Binom}(X_i | \mu_k, N_i)}{\sum_j \pi_k \text{Binom}(X_i | \mu_k, N_i)} \quad (9)$$

Furthermore, based on $\gamma_k$ we can identify the informative SNP sites in the form of $AA_{AB}$.

C. Determination of the Zygosity Status from Informative SNP Sites

In twin pregnancies, we can apply the above algorithm to estimate the apparent fractional fetal DNA concentration and to identify SNP sites that belong to the maternal-fetal mixed genotype $AA_{AB}$. In this situation, $AA_{AB}$ has a different implication from that in singleton pregnancy. For the monozygotic twins, the deduction of the maternal-fetal mixed genotype of $AA_{AB}$ signifies the fetal genotype of AB in both fetuses. For dizygotic twins, $AA_{AB}$ includes three latent groups resulting from different genetic contexts, AA/AA/AB (mother/fetusI/fetusII), AA/AB/AA and AA/AB/AB, respectively. Since we cannot distinguish AA/AA/AB from AA/AB/AA based only on the sequencing data, we mathematically fuse the two former categories into one, and there would only be two effective latent categories, AA/AA/AB and AA/AB/AB, respectively, in order to perform the following analysis.

The modality (i.e. whether there are one or two modes) of the fractional fetal DNA concentrations ($\hat{f}_1$ per SNP site or per block or per chromosome in plasma) for the whole genome (or targeted regions of interest) in maternal plasma is determined by the twins' zygosity status. For twins, two modes may occur for a dizygotic status, where one of those modes may actually be comprised of two sub-nodes (e.g. as shown in FIG. 9), when the fetuses contribute different percentages of fetal DNA.

To elucidate the modality of the genetic makeup, we fit a two-component Gaussian Mixture Model (GMM) to the distribution of $\hat{f}_i$:

$$\hat{f}_i = 2 \times \hat{\mu}_i \quad (10)$$

$$P(\hat{f}_i) = \Sigma_{m=1}^{M} \lambda_m N(\hat{f}_i | \varnothing_m, \sigma^2_m) \quad (11)$$

where $\lambda_m$ are the mixed proportions fulfilling $\Sigma_{m=1}^{M} \lambda_m = 1$ and $0 \leq \lambda_m$ for m=1, ..., M (where M is the maximum number of possible peaks). When the fetuses contribute equal amounts of DNA into the maternal plasma, M equals to the number of fetuses, i.e. 2 for twin pregnancy. $\varnothing_m$ and $\sigma^2_m$ are the mean and variance of normal distribution.

We estimate the mixture components in model (11) using a standard expectation-maximization (EM) algorithm (McLachlan G J and Krishnan T. The EM Algorithm and Extensions. New York: Wiley; 1997). In the algorithm, we put two additional constraints when we identify the two components:
1) $\lambda_m \geq 0.2$, where $\lambda_m$ represents the size of peak m;
2) $\hat{f}_1 - \hat{f}_2 >= \sqrt{\Sigma_{m=1}^{M} \lambda_m \sigma^2_m}$, where $\hat{f}_1 - \hat{f}_2$ indicates the distance between the two peaks.

D. Results

We recruited one dichorionic diamniotic (DCDA) twin pregnancy and one monochorionic diamniotic (MCDA) twin pregnancy for our study. For the DCDA case, blood samples were taken from the mother at 17 weeks of gestation. Cord blood from each twin was stored for the study. For the MCDA case, blood samples were taken from the mother at 12 weeks of gestation. A portion of the chorionic villus sample (CVS) DNA was stored for the study.

To perform SNP genotyping, DNA extracted from maternal buffy coat and cord blood or CVS sample from the twins were genotyped with the Affymetrix Genome-Wide Human SNP Array 6.0 system. The SNPs were classified into different categories based on the homozygosity/heterozygosity status in the mother and each fetus (table 1200 of FIG. 12A and table 1220 of FIG. 12B). The concordance of genotype for Twin I and Twin II indicates that the DCDA case is dizygotic (table 1240 of FIG. 12C). Table 1200 shows the genotyping results for the DCDA case. Table 1220 shows the genotyping results for the MCDA case. Table 3 shows the concordance for Twin I and Twin II in the DCDA case.

Sequencing of plasma DNA was performed as follows. DNA extracted from maternal plasma was target enriched using, for illustration purpose, the Agilent SureSelect technology and then sequenced by the Illumina Hi-Seq standard paired-end protocol, 50 bp for each end, on extracted DNA fragments (203-209 million) equivalent to an average of 138-143 fold coverage for the targeted regions totaling 5.5 Mb in size. The targeted regions included chr1 (0.33 Mb), chr2 (0.30 Mb), chr3 (0.62 Mb), chr4 (0.32 Mb), chr5 (0.33 Mb), chr7 (0.31 Mb), chr8 (0.62 Mb), chr9 (0.31 Mb), chr12 (0.05 Mb), chr13 (0.30 Mb), chr15 (0.33 Mb), chr17 (0.66 Mb), chr19 (0.35 Mb), chr20 (0.34 Mb) and chr22 (0.30 Mb). Other target enrichment technologies, such as the Roche NimbleGen platform and PCR-based technologies (e.g. using the RainDance platform) can also be used.

The apparent fractional fetal DNA concentration was determined across each chromosome. The apparent fractional fetal DNA concentration in the maternal plasma was calculated through the genotypes in combination with the sequencing data. FIG. 12D shows the apparent fractional fetal DNA concentrations calculated based on the genotypes in conjunction with the sequencing data (mother is AA and at least one of fetuses is AB). The results for each chromosome were relatively constant for the MCDA case with a SD of 1.52, while the DCDA case exhibited more fluctuations, with the SD almost doubled to 3.36 (table 1260 of FIG. 12D). For MCDA, fractional fetal DNA concentration was 16.35%. For DCDA, fractional fetal DNA concentration of fetus I was 12.35% (AA/AB/AA) and the fractional fetal DNA concentration of fetus II was 13.60% (AA/AB/AA). The combined fractional fetal DNA concentration was 22.45% (AA/AB/AB) and the apparent fractional fetal DNA concentration was 18.82%.

In order to investigate whether we could distinguish zygosity directly from targeted sequencing data, we performed the deductive SNP calling analysis and then calculated the fetal DNA concentration. FIG. 12E shows the apparent fractional fetal DNA concentration calculated by deductive SNP calling analysis. The results showed a high concordance with the estimates based on the genotypes in conjunction with the sequencing data (Pearson's correlation coefficient 0.8 and 0.8 for DCDA and MCDA, respectively) (table 1280 of FIG. 12E). Furthermore, the SDs allowed us to distinguish the dizygotic twins from monozygotic twins directly (2.14 and 1.10 for dizygotic twins and monozygotic twins, respectively).

For the global distribution of apparent fractional fetal DNA concentrations, we divided the target genome region into multiple blocks (432 and 445 for DCDA and MCDA, respectively) while each block was constructed by including more than 5 neighboring SNPs with distance less than 50 kb. Then we calculated the apparent fractional fetal DNA concentration for each block and drew the distribution of fetal DNA concentration. We used the two-component Gaussian mixture model to fit distribution of fractional fetal DNA concentration per block.

Figure 13:
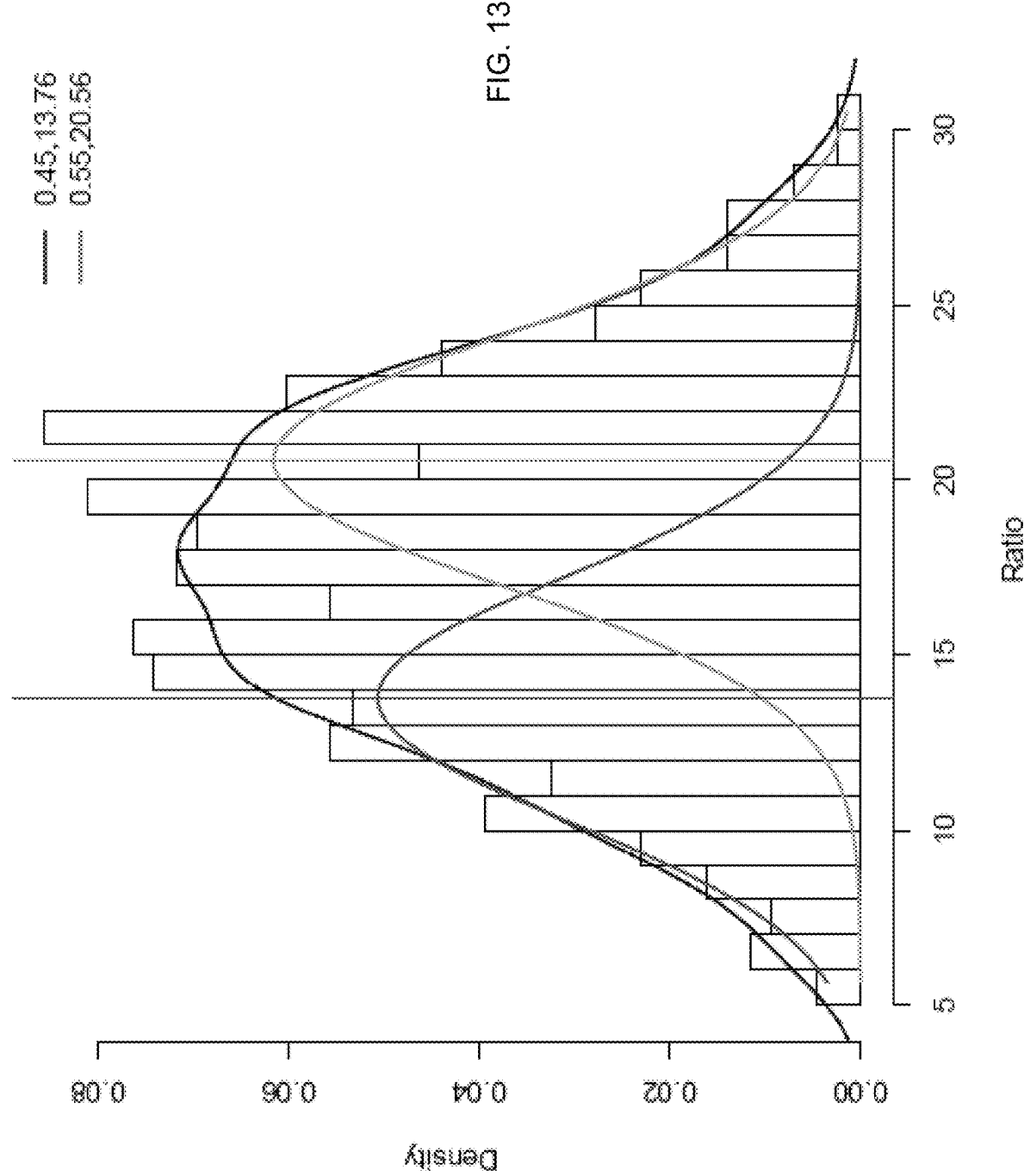
FIG. 13 shows the identification of two distinct peaks for a dizygotic pregnancy.
Figure 14:
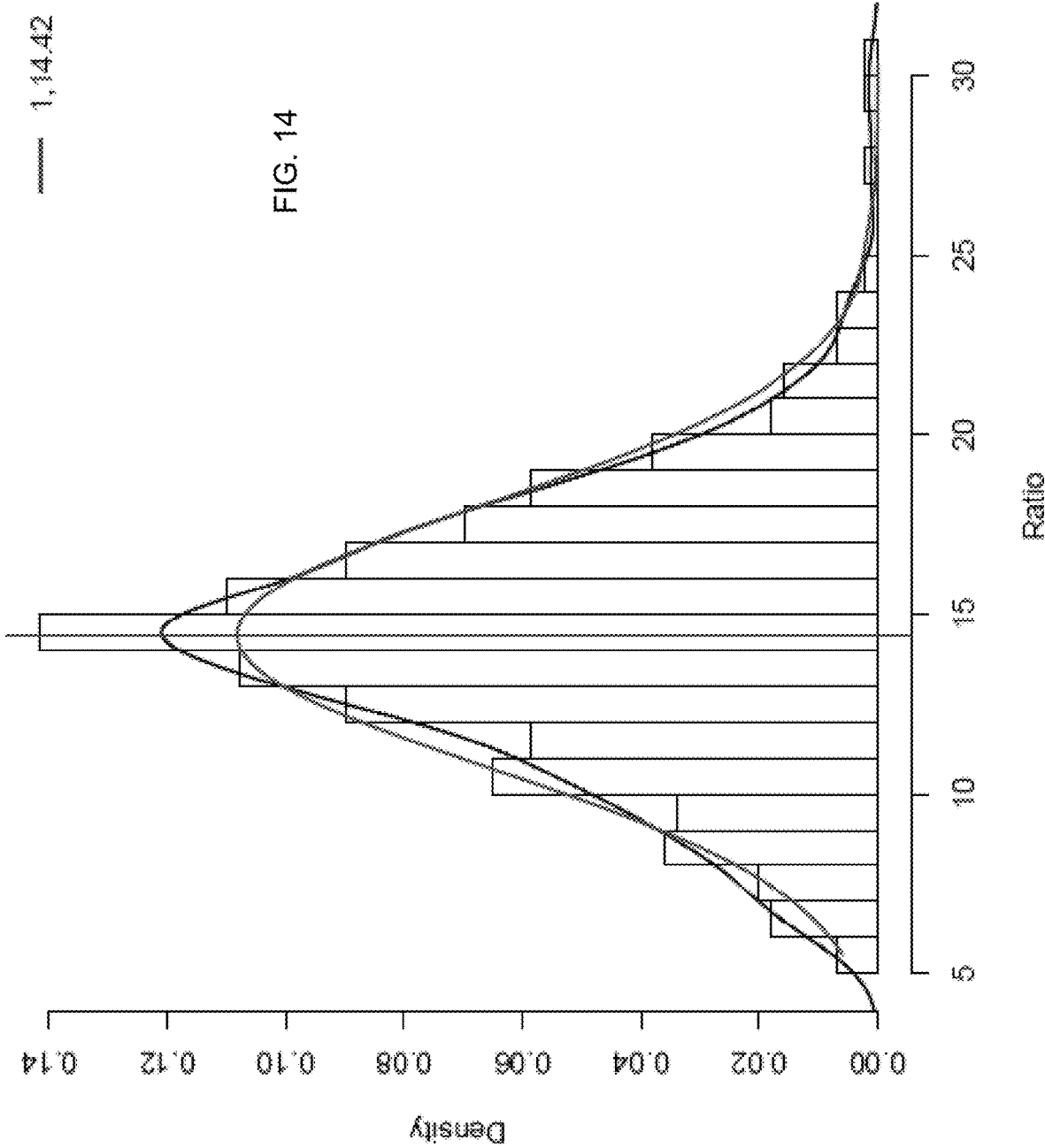
FIG. 14 shows the identification of one peak for a monozygotic pregnancy.

As a result, for the DCDA case, we could identify two distinct peaks from the distribution (FIG. 13), while for the MCDA case, we only obtained 1 peak (FIG. 14). Therefore the dizygotic twins can be distinguished from monozygotic twins through the Gaussian mixture model.

In another embodiment, we simulated two distributions of fractional fetal DNA concentration for monozygotic twins and dizygotic twins, respectively, in silico. Subsequently, the real fractional fetal DNA distributions were compared to the simulated fractional fetal DNA distributions to deduce the zygosity status by determining which of the simulated distributions was closer to the real fractional fetal DNA distribution. Embodiments can also be used for pregnancies involving three or more fetuses by changing the value of M in equation (11).

In conclusion, by massively parallel sequencing of maternal plasma DNA, we found significant difference between the monozygotic twins and dizygotic twins in term of the apparent fractional fetal DNA concentration per SNP or per block or per chromosome. This technology has the advantages that it is noninvasive, and also more reliable than the morphological observation by ultrasound scanning. In other embodiments, other statistical models, e.g. a hidden Markov model, can also be used for determining whether there is one or more peaks of fetal DNA concentrations.

V. Variation of Fractional Fetal DNA Concentration

Figure 15:
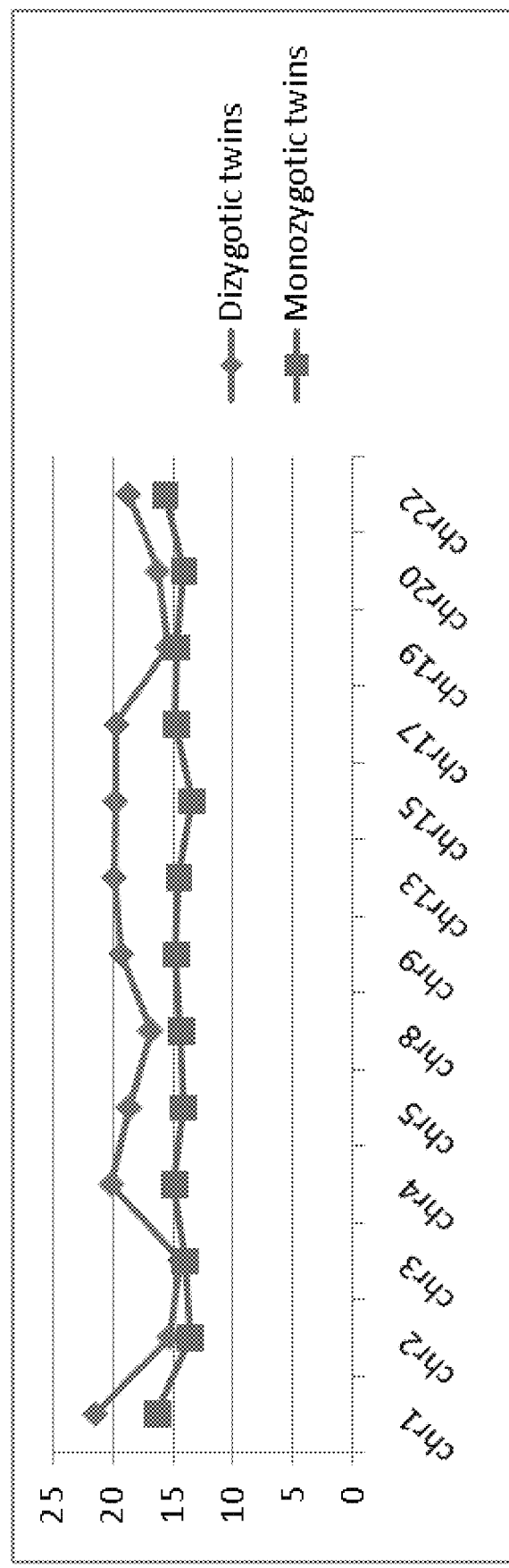
FIG. 15 shows the plasma fractional fetal DNA concentrations for different chromosomal regions for pregnant women carrying monozygotic and dizygotic twins.

By determining the fractional fetal DNA concentrations at different chromosomal regions, we can determine if there is only one or more than one fetal DNA concentration. The plasma fractional fetal DNA concentrations for different chromosomal regions for pregnant women carrying monozygotic and dizygotic twins are shown in FIG. 15. For the pregnant women carrying a pair of monozygotic twins, the fractional fetal DNA concentrations are consistent across different chromosomal regions. In contrast, in the pregnant woman carrying a pair of dizygotic twins, there are increased variations between the fractional fetal DNA concentrations across different chromosomes. Such variations are comparable to the increased standard deviation (SD) shown above for dizygotic fetuses.

In another embodiment, we used a fixed number of SNPs for calculating the apparent fractional fetal DNA concentrations across different chromosomal regions. In principle, the apparent fractional fetal DNA concentration would show a fluctuation across different genomic regions in pregnant women carrying dizygotic twins whereas the apparent concentration would be stable across different genomic regions in pregnant women carrying monozygotic twins. To determine if the fluctuation in fractional concentration is due to stochastic variation with monozygotic twins or the presence of a different fractional fetal DNA concentration with dizygotic twins, we have performed a simulation analysis to determine the level of stochastic variation assuming the presence of a pair of monozygotic twins (FIG. 16)

The simulation is performed based on the following assumptions: (a) There are a pair of monozygotic twins; (b) The overall fractional concentration of all regions is used as the fractional concentration of each tested region; (c) The sequenced depth of the SNPs in each tested region is equal to the average sequenced depth of all regions; and (d) The distribution of SNP alleles following the binomial distribution.

Figure 16:
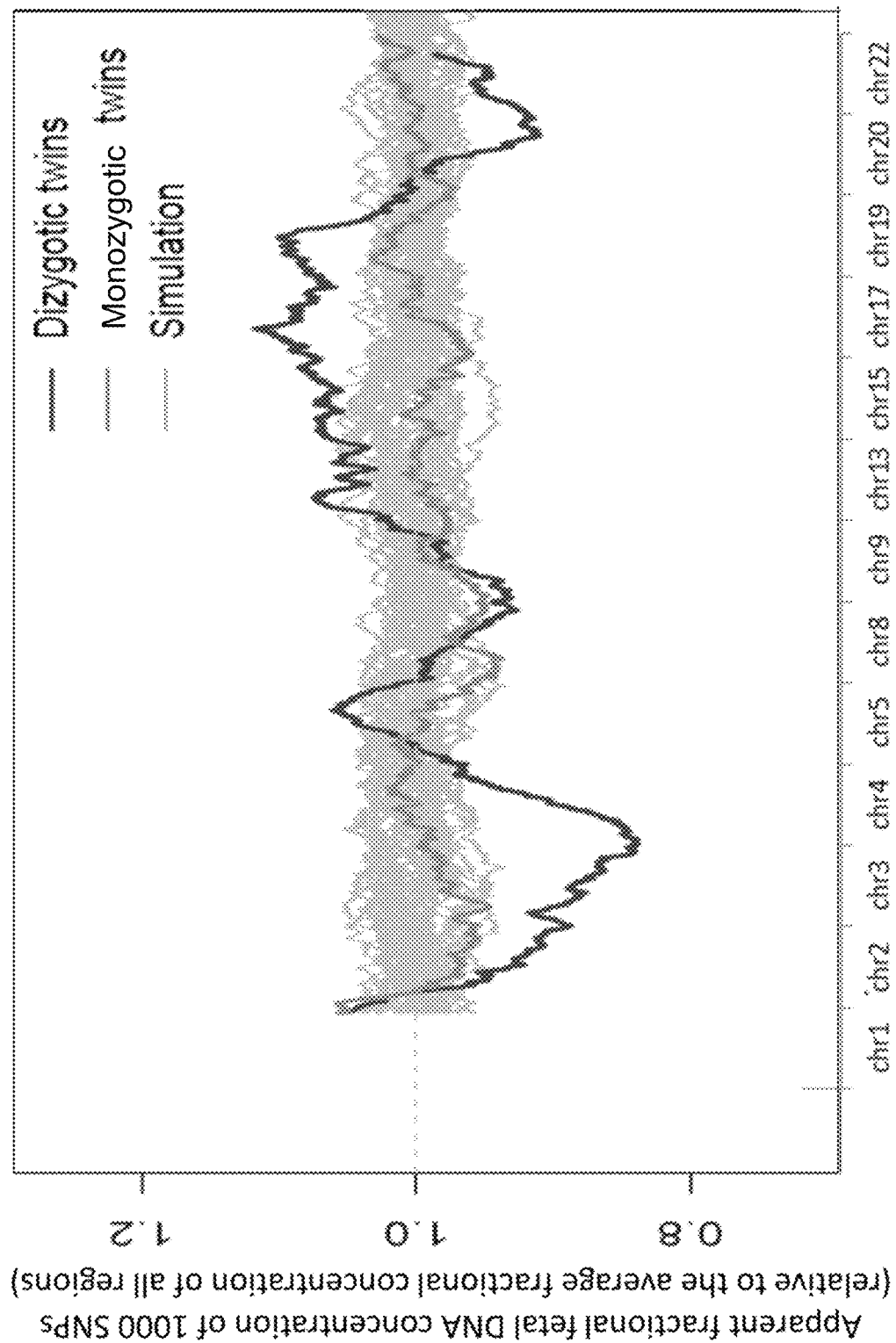
FIG. 16 shows a simulation analysis to determine the level of stochastic variation assuming the presence of a pair of monozygotic twins.

In FIG. 16, the relative apparent fractional fetal DNA concentration was calculated as a running total based on the allelic counts of 1000 consecutive SNPs. The relative apparent fractional concentration was calculated by dividing the local regional concentration for the 1000 SNPs by the average fractional fetal DNA concentration of all regions. The green line represents the results for the mother carrying a pair of monozygotic twins and the red line represents the results for the mother carrying a pair of dizygotic twins. The shaded area in grey represents the results of 1000 different simulations as described above. We can see the green line fluctuates within the shaded area indicating that the fluctuation in fractional concentration is within the predicted variation for a pair of monozygotic twins. On the other hand, the red line fluctuate beyond the shaded area indicating that the fluctuation of the fractional concentration cannot be explained by the stochastic variation alone and, hence, suggests that the pair of twins are dizygotic.

VI. Triplets and Higher

The methods described above can also be used to determine if all of the fetuses in a triplet or a higher multiple pregnancy are genetically identical or at least one of the fetuses is genetically different from the others. In triplet or higher multiple pregnancies, as evidenced for example by ultrasound, if the two paternal haplotypes are detectable in the maternal plasma sample, it would indicate at least one of the fetuses is different from the other fetuses. For the analysis of the fractional fetal DNA concentration, the method of deducing the information SNPs would not be altered. After identification of the informative SNPs and the calculation of the fractional fetal DNA concentrations for different genomic regions, the zygosity status of the fetuses can be determined by the formulas given above with the parameters in the formulas changed accordingly.

Figure 17:
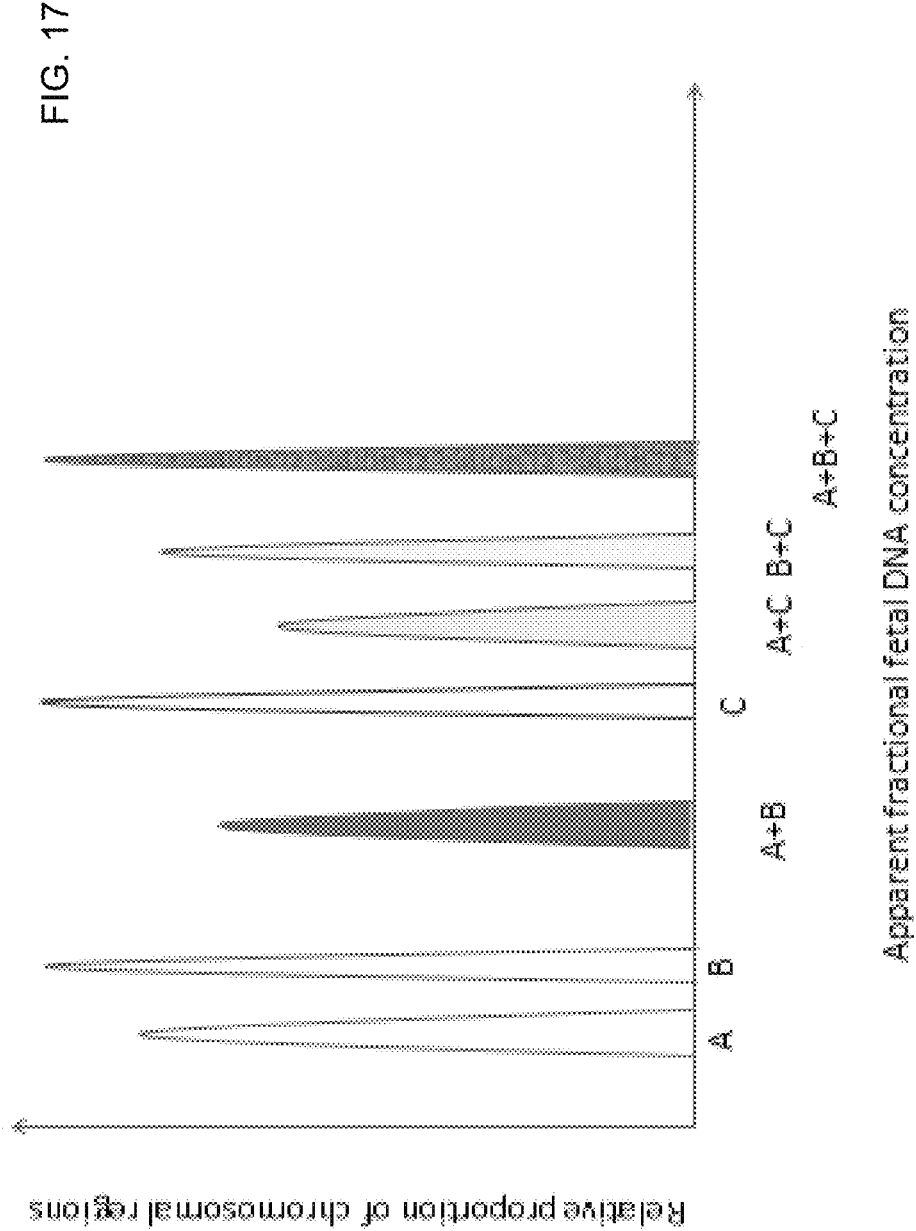
FIG. 17 shows a histogram illustrating a number of possible peaks for three fetuses (fetuses A, B and C) according to embodiments of the present invention.

For triplets and higher, the number of possible peaks M for the multi-component mixture model can be determined as follows. When there are 3 or more fetuses, the calculation of M would be much more complicated. FIG. 17 shows a histogram illustrating a number of possible peaks for three fetuses (fetuses A, B and C) according to embodiments of the present invention. These three fetuses are different genetically and they contribute different amounts of DNA to the maternal plasma. The unfilled peaks represent the chromosomal regions where only one fetus is heterozygous. The peaks with one color represent the chromosomal regions where two fetuses are heterozygous. The filled peaks with different patterns represent chromosomal regions where all the three fetuses are heterozygous. Therefore, there will be a total of 6 peaks.

The relationship between the number of fetuses (N) and the number of peaks (M) would be $$M = \sum_{i=1}^{N} C_i^N.$$

Practically, it would not be necessary to identify all the peaks when all of the fetuses contribute different amounts of DNA to the maternal plasma. However, if all the fetuses contribute equal amounts of DNA to the maternal plasma, M would be equal to N.

VII. Examples

The following are hypothetical examples for the determination of the lowest fractional fetal concentration contributed by a fetus or a number of monozygotic fetuses. Regarding the first example, the determination of fractional fetal DNA concentrations of different fetuses in a multiple pregnancy is useful for adjusting the sensitivity of prenatal diagnostic tests based on the analysis of maternal plasma (also see paragraph 134). In such an application, the lowest fractional fetal DNA concentration contributed by any one of the genetically different fetuses or the combined fetal DNA concentration from two or more genetically identical fetuses, whichever is lower, can be used for guiding whether the sensitivity of the diagnostic test is sufficient to detect a fetal genetic abnormality, e.g. fetal aneuploidy. In the example shown in FIG. 17, the peak contributed by fetus A represents the lowest apparent fetal DNA concentration.

In one embodiment, the lowest fractional fetal DNA concentration can be determined by analyzing a number of informative SNPs at which the mother is homozygous and the father is heterozygous. These SNPs are preferably located on a number of different chromosomes or chromosomal regions. The apparent fractional fetal DNA concentration at each of these SNPs is calculated by the number of DNA fragments carrying the fetal-specific allele and the allele shared between the mother and the fetus. At any SNP locus in which only the fetus contributing the lowest amount of DNA into the maternal plasma is heterozygous but other fetuses are homozygous, the apparent fractional fetal DNA concentration would become the lowest amongst all the SNP loci analyzed. Therefore, the lowest fractional fetal DNA concentration determined in these SNP loci can be used as an estimate of the lowest amount of fetal DNA contributed by any of the genetically different fetuses.

In another embodiment, the determination of the fractional concentration of DNA at a SNP locus can be performed using the digital analysis of selected regions (DANSR) on SNP loci (Sparks A B et al. *Am J ObstetGynecol* 2012;doi: 10.1016/j.ajog.2012.01.030). The digital counting of fetal-specific and shared alleles located on one or more chromosomes can be used for estimating the apparent fractional concentration at each of the SNP loci. Alternatively, the allelic count information on multiple SNP loci located on the same chromosomal region can be analyzed together to indicate the apparent fractional fetal DNA concentration at the respective chromosomal region. The chromosomal region exhibiting the lowest apparent fetal DNA concentration can be used to indicate the lowest fetal DNA contributed by any of the fetuses. In other embodiments, the determination of fractional concentration at different SNP loci can be performed using real-time PCR, mass spectrometry analysis (for example by the Sequenom MassARRAY system) and digital PCR analysis.

The number of SNPs loci to be analyzed should be sufficiently large to ensure that for a pregnancy involving at least one pair of dizygotic twins, at least one of the loci analyzed, only the fetus (or a combination of monozygotic fetuses) contributing to the lowest amount of DNA to the maternal plasma would be heterozygous but the other fetuses would be homozygous for the maternal allele. For example, more than 100 potentially informative SNPs should be analyzed. In addition, a sufficiently large amount of DNA fragments should be analyzed for each potentially informative SNP locus to ensure that the fetal-specific allele is detected.

The second example provides a description of a process according to an embodiment. 10 mL of maternal peripheral blood sample is taken from a pregnant woman known to be carrying twin fetuses by ultrasound. The blood sample is fractionated into plasma and blood cells. The plasma is harvested and the DNA is extracted. The maternal plasma DNA is then amplified in a series of 10 multiplex PCRs. Each PCR allows the amplification of 20 SNP loci, distributed in different genomic regions. Thus, a total of 200 SNP loci would be analyzed in this example.

The PCR products from each of the multiplex PCRs are analyzed by a primer extension assay and the extension products are analyzed, e.g., by a Sequenom MassARRAY system. Each primer extension assay followed by the Sequenom MassARRAY analysis will reveal mass spectrometry peaks corresponding to the alleles of each of the SNP loci. The relative heights of the peaks will indicate the relative amounts of each of the SNP alleles. For SNPs for which both the pregnant mother and her fetuses are homozygous for the same allele, only one peak, corresponding to that allele, will be seen on the mass spectrometry readout. For SNPs for which the pregnant mother is heterozygous, two peaks of approximately equal heights, corresponding to both alleles of the SNPs, will be seen on the mass spectrometry readout. For SNPs for which the pregnant mother is homozygous, and for which at least one of the fetuses is heterozygous, one large peak (corresponding to the mother's allele) and one small peak (corresponding to the fetal allele not present in the mother's genome) will be seen on the mass spectrometry readout. The relative size of the latter two peaks will allow a measurement of the fetal DNA percentage (i.e. the fractional fetal DNA concentration).

In one embodiment using a particular combination of SNP loci, the proportion of SNPs exhibiting one large (corresponding to the maternal allele) and one small (corresponding to the fetal-specific allele) will be, for example, 6%. If the twin fetuses are monozygotic, then the fractional fetal DNA concentrations measured by these 6% of SNPs should be relatively close to each other. The closeness can be measured for example by the standard deviation (SD). If the twin fetuses are dizygotic, then the 6% of SNPs can be divided into two groups. For the first group, the two fetuses would both, just by chance, heterozygous. For the second group, one of the fetuses would be homozygous and the other would be heterozygous, also just by chance. The fractional fetal DNA concentrations measured by one or more SNPs in the first group would be larger than that measured by one or more SNPs in the second group. The SNPs chosen for such analysis can be chosen to be most informative for a particular population.

As an alternative to mass spectrometry, the analysis described in this example can be performed using comparable methods known to those skilled in the art. One example is the performance of an amplification procedure on the SNP loci, followed by massively parallel sequencing. One variant of this strategy is the digital analysis of selected regions (DANSR) (Sparks A B et al. *Am J ObstetGynecol* 2012;doi: 10.1016/j.ajog.2012.01.030). Another example is microdroplet digital PCR, such as using the QuantaLife platform or the RainDance platform (Zhong Q et al. *Lab Chip* 2011; 11: 2167-2174). Yet another example is to use microfluidics digital PCR. The multiplexing of such assays would increase the throughput of such analysis.

VIII. Computer System

Figure 18:
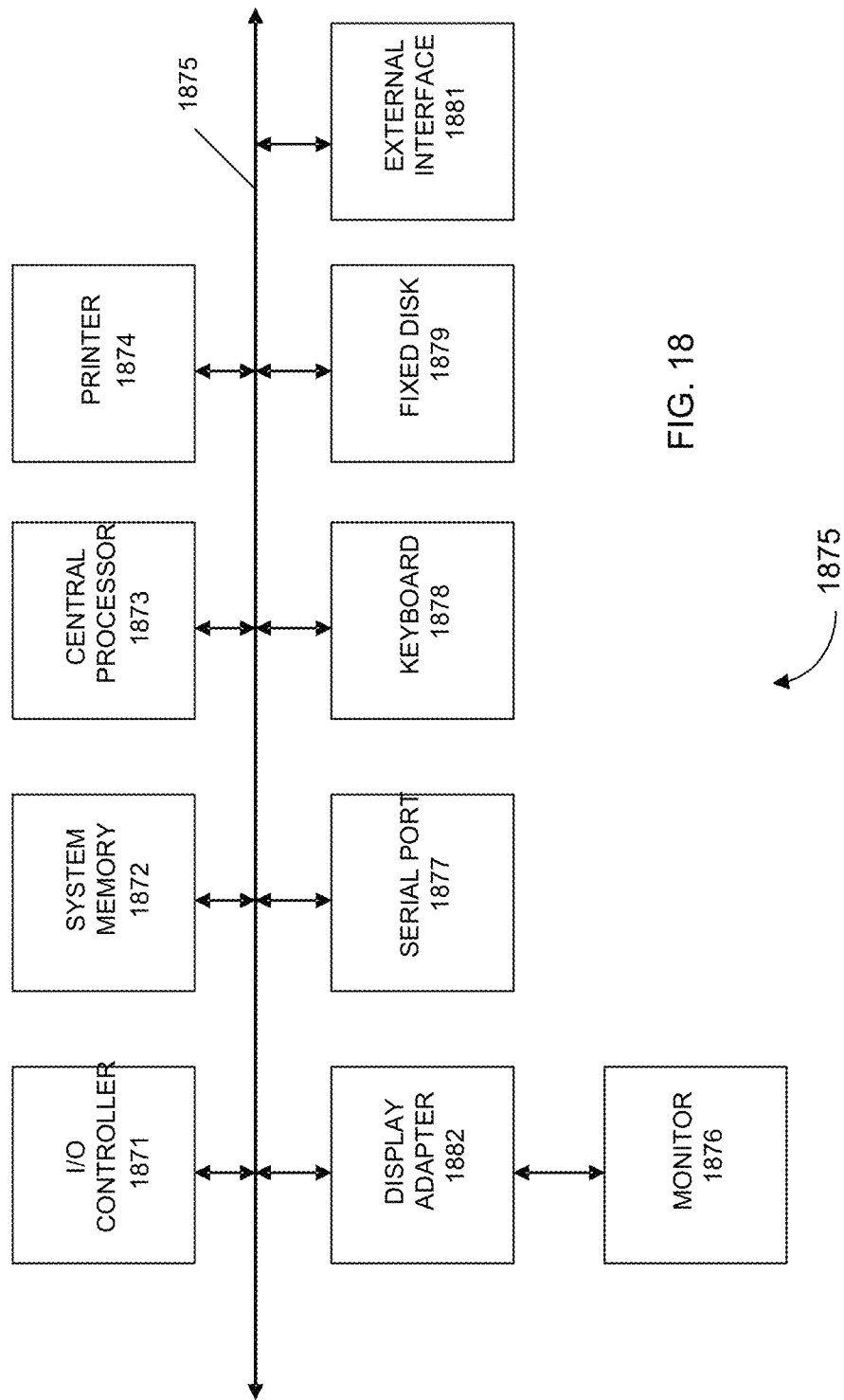
FIG. 18 shows a block diagram of an example computer system 1800 usable with system and methods according to embodiments of the present invention.

Any of the computer systems mentioned herein may utilize any suitable number of subsystems. Examples of such subsystems are shown in FIG. 18 in computer apparatus 1800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 18 are interconnected via a system bus 1875. Additional subsystems such as a printer 1874, keyboard 1878, fixed disk 1879, monitor 1876, which is coupled to display adapter 1882, and others are shown. Peripherals and input/output (I/O) devices, which couple to I/O controller 1871, can be connected to the computer system by any number of means known in the art, such as serial port 1877. For example, serial port 1877 or external interface 1881 can be used to connect computer system 1800 to a wide area network such as the Internet, a mouse input device, or a scanner. The interconnection via system bus 1875 allows the central processor 1873 to communicate with each subsystem and to control the execution of instructions from system memory 1872 or the fixed disk 1879, as well as the exchange of information between subsystems. The system memory 1872 and/or the fixed disk 1879 may embody a computer readable medium. Any of the values mentioned herein can be output from one component to another component and can be output to the user.

A computer system can include a plurality of the same components or subsystems, e.g., connected together by external interface 1881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method for analyzing a biological sample of a female pregnant with a plurality of fetuses to determine whether at least two fetuses of a pregnant female are dizygotic, the biological sample comprising fetal and maternal DNA, the method comprising:
    obtaining a blood sample from the pregnant female;
    harvesting plasma or serum from the blood sample to obtain the biological sample comprising fetal and maternal cell-free DNA fragments;
    enriching the biological sample for DNA fragments in a set of chromosomal regions;
    performing massively parallel sequencing of DNA fragments in the enriched biological sample, thereby analyzing the fetal and maternal cell-free DNA fragments to obtain sequence reads, wherein the sequenced DNA fragments are from at least seven independent chromosomal regions;
    aligning, by a computer system, the sequenced reads to a reference human genome to identify locations and alleles of the DNA fragments, thereby obtaining data about alleles of the DNA fragments, wherein:
        the data provide information about amounts of the alleles of the fetal and maternal cell-free DNA fragments, and
        aligning the sequenced reads to the reference human genome to identify locations and alleles of the DNA fragments comprises identifying locations and alleles of at least two million DNA fragments;
    determining, by the computer system, a genotype of the pregnant female at each of one or more first loci within a first chromosomal region, the pregnant female being homozygous at each of the one or more first loci or being heterozygous at each of the one or more first loci;
    for each first locus of the one or more first loci:
        identifying, by the computer system, a primary allele and a secondary allele in the biological sample using the data, wherein the primary allele is more abundant than the secondary allele at the first locus in the biological sample;
    determining, by the computer system at the one or more first loci, a first amount of the one or more primary alleles and/or a second amount of the one or more secondary alleles in the biological sample using the data, the first amount corresponding to a quantity of DNA fragments having the one or more primary alleles in the biological sample, and the second amount corresponding to a quantity of DNA fragments having the one or more secondary alleles in the biological sample, wherein:
        at least one of the first amount and the second amount includes fetal DNA in the biological sample, and
        the first amount and/or the second amount are amounts of the aligned sequenced reads;
    obtaining, by the computer system, a normalized parameter for the first amount or the second amount;
    calculating, by the computer system, six or more additional normalized parameters for six or more other chromosomal regions using one or more amounts of alleles in the biological sample at one or more other loci in each chromosomal region of the six or more other chromosomal regions, the at least seven independent chromosomal regions including the first chromosomal region and the six or more other chromosomal regions, wherein the pregnant female is homozygous at all of the one or more other loci and the one or more first loci or is heterozygous at all of the one or more other loci and the one or more first loci, and wherein each of the one or more other loci has a primary allele and a secondary allele, wherein the normalized parameter and the six or more additional normalized parameters are each normalized by a correlated procedure;
    computing, by the computer system, a variance in the values of the normalized parameter and the six or more additional normalized parameters;
    comparing the variance to a threshold value;
    determining that at least two fetuses of the pregnant female are dizygotic when the variance is above the threshold value; and
    outputting, by the computer system, the determination of the dizygosity of the at least two fetuses of the pregnant female, wherein
    the method is noninvasive to the fetus and the placenta.

2. The method of claim 1, further comprising:
    at each of the first loci, detecting the primary allele and the secondary allele in the biological sample.

3. The method of claim 1, wherein obtaining the normalized parameter includes:
    determining a third amount of one or more sequences from one or more loci within a different chromosomal region; and
    using the third amount and the first amount or the second amount to calculate the normalized parameter.

4. The method of claim 1, wherein obtaining the normalized parameter includes:
   determining, at the one or more first loci, the first amount of the one or more primary alleles and the second amount of the one or more secondary alleles in the biological sample;
   determining a first parameter from the first amount and the second amount, the first parameter providing a relative amount between the first amount and the second amount; and
   using the first parameter as the normalized parameter of the first amount.

5. The method of claim 1, wherein obtaining the normalized parameter includes:
   performing, using a calibrated process, the determining of the first amount of the one or more primary alleles and/or the second amount of the one or more secondary alleles in the biological sample; and
   using the first amount or the second amount as the normalized parameter.

6. The method of claim 1, wherein the one or more loci includes the locus of the RHD gene, the mother being homozygous for an allele represented by the absence of the RHD gene, and wherein at least one of the fetuses is RhD-positive.

7. The method of claim 1, wherein the variance is the standard deviation in the normalized parameters.

8. The method of claim 1, wherein the at least two fetuses are determined to be monozygotic when the variance is below the threshold value.

9. The method of claim 1, further comprising displaying, by the computer system, a result that at least two fetuses of the pregnant female are dizygotic when the variance is above the threshold value.

10. The method of claim 1, wherein the sequencing of the fetal and maternal cell-free DNA fragments includes random sequencing across the autosomes.

11. The method of claim 1, wherein the DNA fragments comprise at least 203 million DNA fragments.

12. The method of claim 1, wherein the method for analyzing the biological sample of the female pregnant with the plurality of fetuses is part of a process that decreases a risk of harm compared to an amniocentesis for at least one of the plurality of fetuses or the female.

13. The method of claim 1, wherein the sequencing of the DNA fragments is at least at 138 fold coverage for the at least seven independent chromosomal regions.

14. The method of claim 1, wherein obtaining the blood sample from the pregnant female comprises obtaining the blood sample from the pregnant female at 17 weeks of gestation or later.

15. A method for analyzing a biological sample of a female pregnant with a plurality of fetuses to determine whether at least two fetuses of a pregnant female are dizygotic, the biological sample comprising fetal and maternal DNA, the method comprising:
   obtaining a blood sample from the pregnant female;
   harvesting plasma or serum from the blood sample to obtain the biological sample;
   performing massively parallel sequencing of DNA fragments in the biological sample, thereby analyzing DNA fragments in the biological sample to obtain sequence reads, wherein the sequenced DNA fragments are from at least seven independent chromosomal regions;
   aligning, by a computer system, the sequenced reads to a reference human genome to identify locations and alleles of the DNA fragments, thereby obtaining data about sequences of the DNA fragments, wherein:
      the data provide information about amounts of the sequences of the DNA fragments, and
      wherein aligning the sequenced reads to the reference human genome to identify locations and alleles of the DNA fragments comprises identifying locations and alleles of at least two million DNA fragments;
   determining, by the computer system at one or more first loci within a first chromosomal region, a first amount of one or more fetal-specific sequences in the biological sample, the first amount corresponding to a quantity of DNA fragments having the one or more fetal-specific sequences in the biological sample, the first amount being an amount of the aligned sequenced reads;
   obtaining, by the computer system, a normalized parameter for the first amount; and
   comparing the normalized parameter to a cutoff value to determine if the normalized parameter is statistically different from an expected value that is expected when the fetuses are genetically identical for the first chromosomal region, the expected value corresponding to the obtained normalized parameter and being obtained from a measurement of the biological sample;
   when the normalized parameter is statistically different from the expected value, determining a classification of the at least two fetuses of the pregnant female as being dizygotic based on the normalized parameter being statistically different from the expected value for the first chromosomal region, and
   outputting, by the computer system, the classification of the dizygosity of the at least two fetuses of the pregnant female, wherein
   the method is noninvasive to the fetus and the placenta.

16. The method of claim 15, wherein the fetal-specific sequence is on the Y chromosome.

17. The method of claim 15, wherein the fetal-specific sequence is the RHD gene, and wherein the pregnant female is RhD-negative.

18. The method of claim 15, wherein the expected value is a fetal DNA concentration in the biological sample.

19. The method of claim 15, wherein the one or more first loci are within a first chromosomal region, the method further comprising:
   determining, at one or more second loci, a second amount of one or more additional fetal-specific sequences in the biological sample, the second loci being within a second chromosomal region different than the first chromosomal region;
   obtaining an additional normalized parameter for the second amount; and
   using the additional normalized parameter to obtain the expected value.

20. The method of claim 18, further comprising:
   measuring the fetal DNA concentration using one or more epigenetic markers.

21. The method of claim 20, wherein the one or more epigenetic markers include one or more DNA methylation markers.

22. The method of claim 18, further comprising:
   calculating the fetal DNA concentration using genetic markers by:
      measuring a third amount of DNA fragments having a fetal-specific sequence selected from one or more fetal-specific sequences, wherein all of the fetuses have the fetal-specific sequence;
      obtaining a normalized value for the third amount; and
      using the normalized value as the fetal DNA concentration.

23. The method of claim 22, wherein the fetuses are all males, and wherein the one or more fetal-specific sequences are on the Y chromosome.

24. The method of claim 22, wherein the fetal-specific sequence is the RHD gene, wherein the mother is RhD-negative, and wherein all of the fetuses are RhD-positive.

25. The method of claim 22, further comprising:
identifying one or more second loci at which the fetuses have a respective first allele and the mother does not have the respective first allele, wherein the fetal-specific sequences are the respective first alleles, wherein obtaining a normalized value for the third amount includes:
measuring a total amount of alleles at the one or more second loci;
calculating the fetal DNA concentration from a ratio of the third amount and the total amount.

26. The method of claim 18, further comprising:
determining a genotype of the pregnant female at each of one or more second loci within a second chromosomal region, the pregnant female being homozygous at each of the one or more second loci or being heterozygous at each of the one or more second loci, wherein each of the second loci exhibits a primary allele and a secondary allele in the biological sample;
measuring, at the one or more second loci, a third amount of the one or more primary alleles and/or a fourth amount of the one or more secondary alleles in the biological sample;
obtaining a second normalized parameter for the third amount or the fourth amount; and
using the second normalized parameter to obtain the expected value.

27. The method of claim 26, wherein the second normalized parameter is used as the expected value.

28. The method of claim 26, further comprising:
calculating additional normalized parameters for other chromosomal regions;
computing a first statistical value from the normalized parameters of a first group of chromosomal regions; and
using the first statistical value as the expected value.

29. The method of claim 28, wherein the primary allele is more abundant than the secondary allele for all of the loci of the chromosomal regions of the first group.

30. The method of claim 28, wherein the first statistical value is a location of a peak in the values of the normalized parameters in a histogram of the normalized parameters for the first group of chromosomal regions.

31. The method of claim 28, further comprising:
computing a second statistical value from the parameters of a second group of chromosomal regions that includes the first chromosomal region,
wherein comparing the normalized parameter to the cutoff value includes:
comparing the second statistical value to the cutoff value.

32. The method of claim 31, further comprising:
identifying the first and second groups of chromosomal regions by analyzing a histogram of the calculated parameters, wherein the first group of chromosomal regions corresponds to a first peak in the histogram and the second group of chromosomal regions corresponds to a second peak in the histogram.

33. A method for analyzing a biological sample of a female pregnant with a plurality of fetuses to determine whether at least two fetuses of the pregnant female are dizygotic, the biological sample comprising fetal and maternal DNA, the method comprising:
obtaining a blood sample from the pregnant female;
harvesting plasma or serum from the blood sample to obtain the biological sample;
measuring a fetal concentration f of fetal DNA in the biological sample;
performing massively parallel sequencing of DNA fragments in the biological sample to obtain sequence reads, wherein at least $(-2/f) \times \ln(0.01)$ DNA fragments are sequenced for each of a plurality of chromosomal regions;
aligning, by a computer system, the sequenced reads to a reference human genome to identify locations and alleles of the DNA fragments, thereby obtaining data about alleles of the DNA fragments, wherein:
the data provide information about amounts of the alleles of the DNA fragments, the amounts are amounts of the aligned sequenced reads corresponding to the alleles, and
aligning the sequenced reads to the reference human genome to identify locations and alleles of the DNA fragments comprises identifying locations and alleles of at least two million DNA fragments;
for each of the plurality of chromosomal regions:
at each of one or more loci in the respective chromosomal region:
detecting, by the computer system, one or more alleles in the biological sample by using the aligned sequenced reads; and
determining, by the computer system, a respective amount of DNA fragments having each detected allele, wherein detecting at least one of the respective amounts includes detecting fetal DNA in the biological sample;
based on the respective amounts of the one or more alleles for each of the plurality of chromosomal regions, determining whether at least two of the fetuses have inherited a different haplotype of the respective chromosomal region from a first parent;
determining a first amount of the chromosomal regions where at least two of the fetuses have inherited a different haplotype from the first parent; and
comparing the first amount to a cutoff value to determine whether at least two of the fetuses are dizygotic, wherein a classification of dizygosity corresponds to the first amount being greater than the cutoff value; and
outputting, by the computer system, the classification of the dizygosity of the at least two fetuses of the pregnant female, wherein
the method is noninvasive to the fetus and the placenta.

34. The method of claim 33, wherein the first amount is a proportion.

35. The method of claim 33, the method further comprising:
determining the two haplotypes of the first parent at a plurality of loci for a first chromosomal region,
wherein determining that at least two of the fetuses have inherited a different haplotype of the first chromosomal region from the first parent includes:
identifying a first locus and a second locus in the first chromosomal region at which the first parent is heterozygous;
detecting in the biological sample a first haplotype of the first parent at the first locus; and detecting in the biological sample a second haplotype of the first parent at the second locus.

36. The method of claim 35, wherein the first parent is the mother, wherein the father is homozygous at the first locus for a first allele, and the mother is heterozygous for the first allele and a second allele at the first locus, the first allele being on the first haplotype and the second allele being on the second haplotype of the mother, wherein detecting in the biological sample the first haplotype of the first parent at the first locus includes:
   determining that the respective amount of the first allele detected at the first locus is greater than the respective amount of the second allele detected at the second locus by a statistically significant amount;
   wherein the father is homozygous at the second locus for a fourth allele, and the mother is heterozygous for a third allele and the fourth allele at the second locus, the third allele being on the first haplotype and the fourth allele being on the second haplotype of the mother, wherein detecting in the biological sample the second haplotype of the first parent at the second locus includes:
      determining that the respective amount of the fourth allele detected at the second locus is greater than the respective amount of the third allele detected at the second locus by a statistically significant amount.

37. The method of claim 35, wherein the first parent is the father, wherein the second parent is homozygous at the first locus for a first allele, and the first parent is heterozygous for the first allele and a second allele at the first locus, wherein detecting in the biological sample the first haplotype of the first parent at the first locus includes:
   detecting in the biological sample the second allele at the first locus.

38. The method of claim 35, wherein the first locus and the second locus are close enough that the probability of recombination between the first locus and the second locus is less than 0.1%.

39. The method of claim 33, wherein the first parent is the father, the method further comprising:
   identifying a first locus in a first chromosomal region where the first parent is heterozygous for a first allele and a second allele, both of which are not present in the second parent at the first locus,
   wherein determining that two of the fetuses have inherited a different haplotype of the first chromosomal region from the first parent includes:
      detecting the first allele and the second allele at the first locus.

40. The method of claim 39, wherein the first allele and the second allele contain different numbers of a short tandem repeat.

41. A method for analyzing a biological sample of a pregnant female to determine whether at least two fetuses of the pregnant female are dizygotic, the biological sample comprising fetal and maternal DNA, the method comprising:
   obtaining a blood sample from the pregnant female;
   harvesting plasma or serum from the blood sample to obtain the biological sample;
   performing massively parallel sequencing of DNA fragments in the biological sample, thereby analyzing DNA fragments to obtain sequence reads, wherein the sequenced DNA fragments are from at least seven independent chromosomal regions;
   aligning, by a computer system, the sequenced reads to a reference human genome to identify locations and alleles of the DNA fragments, thereby obtaining data about alleles of the DNA fragments that cover a plurality of chromosomal regions, wherein:
      the data provide information about amounts of the alleles of the fetal and maternal cell-free DNA fragments, and
      aligning the sequenced reads to the reference human genome to identify locations and alleles of the DNA fragments comprises identifying locations and alleles of at least two million DNA fragments;
   creating a histogram by:
      for each of the plurality of chromosomal regions:
         identifying one or more loci in the respective chromosomal region at each of which a first allele and a second allele are detected in the biological sample;
         determining, by the computer system at the one or more loci, a first amount of DNA fragments having the one or more first alleles and/or a second amount of DNA fragments having the one or more second alleles in the biological sample, wherein
            at least one of the first amount and the second amount includes fetal DNA in the biological sample, and
            the first amount and/or the second amount are amounts of the aligned sequenced reads; and
         obtaining, by the computer system, a normalized parameter for the first amount or the second amount; and
      incrementing, by the computer system, counters based on a number of chromosomal regions with specified values for the normalized parameter, each counter corresponding to a different range of values for the normalized parameter;
   identifying chromosomal regions corresponding to loci at which the mother is homozygous and at least one of the fetuses is heterozygous or corresponding to loci at which the mother is heterozygous and at least one of the fetuses is homozygous, the loci identified based on the locations and alleles of the DNA fragments;
   fitting, by the computer system, a multi-component mixture model to the histogram corresponding to the identified chromosomal regions, the multi-component mixture model including a mixture coefficient for each of a plurality of components; and
   determining whether at least two of the fetuses are dizygotic using at least two of the mixture coefficients; and
   outputting, by the computer system, the determination of the dizygosity of the at least two fetuses of the pregnant female, wherein
      the method is noninvasive to the fetus and the placenta.

42. The method of claim 41, wherein the multi-component mixture model has three components.

43. The method of claim 41, wherein the multi-component mixture model is a Gaussian mixture model.

44. The method of claim 41, further comprising:
   determining genotypes of the fetuses for the one or more loci of a first chromosomal region by identifying the component of the mixture model with a highest overlap with the corresponding normalized parameter for the first chromosomal region.

45. The method of claim 41, wherein at least two of the fetuses are determined to be dizygotic when at least two of the mixture coefficients are above a threshold.

46. The method of claim 41, wherein locations of the peaks of the components of the mixture model are constrained to have a separation gap that exceeds a predetermined value.

47. The method of claim 41, wherein identifying the chromosomal regions includes:
 fitting a linear combination of probability distributions to the histogram for a given fetal DNA percentage of the biological sample; and
 identifying a probability distribution corresponding to loci at which the mother is homozygous and at least one of the fetuses is heterozygous or corresponding to loci at which the mother is heterozygous and at least one of the fetuses is homozygous, wherein the multi-component mixture model is fit to the identified probability distribution.

48. The method of claim 41, further comprising:
 determining the given fetal DNA percentage using one or more epigenetic markers.

49. The method of claim 48, wherein the one or more epigenetic markers include one or more DNA methylation markers.

* * * * *